US010273456B2

(12) United States Patent
Radwanski et al.

(10) Patent No.: US 10,273,456 B2
(45) Date of Patent: Apr. 30, 2019

(54) AUTOMATED METHODS AND SYSTEMS FOR WASHING PLATELET CONCENTRATES

(71) Applicant: Fenwal, Inc., Lake Zurich, IL (US)

(72) Inventors: Katherine Radwanski, Des Plaines, IL (US); Kyungyoon Min, Kildeer, IL (US)

(73) Assignee: FENWAL, INC., Lake Zurich, IL (US)

( * ) Notice: Subject to any disclaimer, the term of this patent is extended or adjusted under 35 U.S.C. 154(b) by 0 days.

(21) Appl. No.: 15/193,397

(22) Filed: Jun. 27, 2016

(65) Prior Publication Data

US 2016/0333315 A1    Nov. 17, 2016

Related U.S. Application Data

(62) Division of application No. 14/110,076, filed as application No. PCT/US2012/032551 on Apr. 6, 2012, now Pat. No. 9,402,866.

(60) Provisional application No. 61/541,793, filed on Sep. 30, 2011, provisional application No. 61/472,952, filed on Apr. 7, 2011.

(51) Int. Cl.
*C12N 5/078* (2010.01)
*A61M 1/02* (2006.01)
*A01N 1/02* (2006.01)
*A61K 35/19* (2015.01)
*A61M 1/36* (2006.01)

(52) U.S. Cl.
CPC ......... *C12N 5/0644* (2013.01); *A01N 1/0226* (2013.01); *A61K 35/19* (2013.01); *A61M 1/0272* (2013.01); *A61M 1/3692* (2014.02); *A61M 1/3696* (2014.02); *A61M 1/0209* (2013.01); *A61M 1/3693* (2013.01); *A61M 2202/0427* (2013.01)

(58) Field of Classification Search
CPC .................................................. A61M 1/0209
See application file for complete search history.

(56) References Cited

U.S. PATENT DOCUMENTS

| 2,786,014 | A | 3/1957 | Tullis |
| 3,629,071 | A | 12/1971 | Sekhar |
| 4,054,488 | A | 10/1977 | Marbach |
| 4,061,537 | A | 12/1977 | Seiler |
| 4,124,598 | A | 11/1978 | Hearst et al. |
| 4,314,025 | A | 2/1982 | McCue |
| 4,405,719 | A | 9/1983 | Crews et al. |
| 4,447,415 | A | 5/1984 | Rock et al. |
| 4,455,299 | A | 6/1984 | Grode |
| 4,572,899 | A | 2/1986 | Walker et al. |
| 4,585,735 | A | 4/1986 | Meryman et al. |
| 4,608,255 | A | 8/1986 | Kahn et al. |
| 4,626,431 | A | 12/1986 | Batchelor et al. |
| 4,626,432 | A | 12/1986 | Hyde et al. |
| 4,695,460 | A | 9/1987 | Holme |
| 4,702,352 | A | 10/1987 | Ingram |
| RE32,874 | E | 2/1989 | Rock et al. |
| 4,828,976 | A | 5/1989 | Murphy |
| 4,923,797 | A | 5/1990 | Babior |
| 4,925,665 | A | 5/1990 | Murphy |
| 4,946,648 | A | 8/1990 | Dichtelmuller et al. |
| 4,961,928 | A | 10/1990 | Holme |
| 4,980,277 | A | 12/1990 | Junnila |
| 4,992,363 | A | 2/1991 | Murphy |
| 4,994,367 | A | 2/1991 | Bode et al. |
| 5,089,146 | A | 2/1992 | Carmen et al. |
| 5,133,932 | A | 7/1992 | Gunn et al. |
| 5,147,290 | A | 9/1992 | Jonsson |
| 5,152,905 | A | 10/1992 | Pall et al. |
| 5,213,813 | A | 5/1993 | Kornecki et al. |
| 5,234,808 | A | 8/1993 | Murphy |
| 5,236,716 | A | 8/1993 | Carmen et al. |
| 5,248,506 | A | 9/1993 | Holme et al. |
| 5,281,392 | A | 1/1994 | Rubinstein et al. |
| 5,300,019 | A | 4/1994 | Bischof et al. |
| 5,344,752 | A | 9/1994 | Murphy |
| 5,358,844 | A | 10/1994 | Stossel et al. |
| 5,360,542 | A | 11/1994 | Williamson, IV et al. |

(Continued)

FOREIGN PATENT DOCUMENTS

DE    3804965 A1    8/1989
DE    43 30 213 A1    3/1995

(Continued)

OTHER PUBLICATIONS

Kalmin, et al. Transfusion, 1982, 22(2):125-127.*
Zhang, et al. Tranfusion, 2008, 48:847-856.*
Ringwald et al. Transfusion, 2006, 46:236-243.*
Shimizu, T., et al., "First Autoclave-Sterilized Platelet-Additive Solution Containing Glucose with a Physiological pH for the Preparation of Plasma-Poor Platelet Concentrates", Vox Sang, vol. 62, 1992, pp. 87-93.
Gulliksson, Hans, "Defining the Optimal Storage Conditions for the Long-Term Storage of Platelets", Transfusion Medicine Reviews, vol. 17, No. 3, Jul. 2003, pp. 209-215.

(Continued)

*Primary Examiner* — Bin Shen
(74) *Attorney, Agent, or Firm* — Cook Alex Ltd.

(57) ABSTRACT

Automated systems and methods for providing platelet concentrates and synthetic storage media with reduced residual plasma volumes are disclosed. The disclosed systems and methods reduce the residual volume of plasma in platelet concentrate to obtain a platelet product having a volume of plasma that is approximately 5% or less of the total platelet product volume. The disclosed systems and methods also reduce the residual volume of plasma in platelet concentrate to obtain a washed platelet product, wherein the volume of plasma in the washed platelet product is approximately 1% or less of the total washed platelet product volume. Storage media for platelets including less than approximately 10% plasma are also disclosed.

12 Claims, 16 Drawing Sheets

(56) References Cited

U.S. PATENT DOCUMENTS

| | | | |
|---|---|---|---|
| 5,376,524 A | 12/1994 | Murphy et al. |
| 5,378,601 A | 1/1995 | Gepner-Puszkin |
| 5,399,268 A | 3/1995 | Pall et al. |
| 5,427,695 A | 6/1995 | Brown |
| 5,439,570 A | 8/1995 | Sessler et al. |
| 5,459,030 A | 10/1995 | Lin et al. |
| 5,462,733 A | 10/1995 | Edelson et al. |
| 5,466,573 A | 10/1995 | Murphy et al. |
| 5,474,891 A | 12/1995 | Murphy |
| 5,480,773 A | 1/1996 | Ogata et al. |
| 5,482,828 A | 1/1996 | Lin et al. |
| 5,484,803 A | 1/1996 | Richter |
| 5,487,971 A | 1/1996 | Holme et al. |
| 5,511,558 A | 4/1996 | Shepard |
| 5,536,238 A | 7/1996 | Bischof |
| 5,538,894 A | 7/1996 | Patscheke et al. |
| 5,554,527 A | 9/1996 | Fickenscher |
| 5,569,579 A | 10/1996 | Murphy |
| 5,601,972 A | 2/1997 | Meryman |
| 5,614,106 A | 3/1997 | Payrat et al. |
| 5,622,867 A | 4/1997 | Livesey et al. |
| 5,629,145 A | 5/1997 | Meryman |
| 5,651,966 A | 7/1997 | Read et al. |
| 5,667,963 A | 8/1997 | Smith et al. |
| 5,712,085 A | 1/1998 | Wollowitz et al. |
| 5,712,086 A | 1/1998 | Horowitz et al. |
| 5,753,428 A | 5/1998 | Yuasa et al. |
| 5,762,867 A | 6/1998 | D'Silva |
| 5,769,839 A | 6/1998 | Carmen et al. |
| 5,834,418 A | 11/1998 | Brazeau |
| 5,868,695 A | 2/1999 | Wolf, Jr. |
| 5,871,459 A | 2/1999 | Muller |
| 5,871,900 A | 2/1999 | Wollowitz |
| 5,899,874 A | 5/1999 | Jonsson |
| 5,906,915 A | 5/1999 | Payrat et al. |
| 5,908,742 A | 6/1999 | Lin et al. |
| 5,922,278 A | 7/1999 | Chapman et al. |
| 5,935,092 A | 8/1999 | Sun et al. |
| 5,951,509 A | 9/1999 | Morris |
| 5,965,349 A | 10/1999 | Lin et al. |
| 6,004,742 A | 12/1999 | Wollowitz et al. |
| 6,017,691 A | 1/2000 | Wollowitz et al. |
| 6,027,657 A | 2/2000 | Min et al. |
| 6,063,624 A | 5/2000 | Kandler et al. |
| 6,114,130 A | 9/2000 | Veriac et al. |
| 6,193,891 B1 | 2/2001 | Kent et al. |
| 6,194,139 B1 | 2/2001 | Wollowitz et al. |
| 6,218,100 B1 | 4/2001 | Wollowitz et al. |
| 6,221,669 B1 | 4/2001 | Livesey et al. |
| 6,251,580 B1 | 6/2001 | Lin et al. |
| 6,277,556 B1 | 8/2001 | Grode et al. |
| 6,277,577 B1 | 8/2001 | Rossau et al. |
| 6,326,197 B1 | 12/2001 | Kandler et al. |
| 6,413,713 B1 | 7/2002 | Serebinnikov et al. |
| 6,482,585 B2 | 11/2002 | Dottori |
| 6,492,103 B1 | 12/2002 | Taylor et al. |
| 6,544,727 B1 | 4/2003 | Hei |
| 6,548,241 B1 | 4/2003 | McBurney et al. |
| 6,566,046 B2 | 5/2003 | Lin et al. |
| 6,653,062 B1 | 11/2003 | DePablo et al. |
| 6,723,497 B2 | 4/2004 | Wolkers |
| 6,743,575 B2 | 6/2004 | Wiggins et al. |
| 6,790,603 B2 | 9/2004 | Ericson et al. |
| 6,828,090 B2 | 12/2004 | Lucas et al. |
| 6,866,992 B2 | 3/2005 | Lin et al. |
| 6,884,228 B2 | 4/2005 | Brown et al. |
| 6,913,932 B2 | 7/2005 | Maples |
| 6,919,172 B2 | 7/2005 | DePablo et al. |
| 6,936,413 B1 | 8/2005 | Bischof et al. |
| 6,994,954 B2 | 2/2006 | Taylor |
| 7,011,938 B2 | 3/2006 | Macey |
| 7,037,642 B2 | 5/2006 | Hei |
| 7,083,910 B2 | 8/2006 | Lucas et al. |
| 7,169,606 B2 | 1/2007 | DePablo et al. |
| 7,202,020 B2 | 4/2007 | Lucas et al. |
| 7,220,747 B2 | 5/2007 | Dumont et al. |
| 7,241,282 B2 | 7/2007 | Stossel |
| 7,255,983 B2 | 8/2007 | Steen |
| 7,264,608 B2 | 9/2007 | Bischof et al. |
| 8,454,548 B2 * | 6/2013 | Ohashi ............ A61M 1/0209 604/4.01 |
| 8,808,978 B2 * | 8/2014 | Pages ............... A61M 1/3693 435/2 |
| 2002/0034722 A1 | 3/2002 | Ericson et al. |
| 2002/0045228 A1 | 4/2002 | Hei |
| 2002/0104808 A1 | 8/2002 | Blasetti et al. |
| 2002/0131958 A1 | 9/2002 | Chapman et al. |
| 2002/0146400 A1 | 10/2002 | Cincotta |
| 2002/0164795 A1 | 11/2002 | Gen |
| 2003/0186213 A1 | 10/2003 | McBurney et al. |
| 2003/0215781 A1 | 11/2003 | DeGroot et al. |
| 2003/0215785 A1 | 11/2003 | Goodrich et al. |
| 2004/0023201 A9 | 2/2004 | McBurney et al. |
| 2004/0038997 A1 | 2/2004 | Macey |
| 2004/0132207 A1 | 7/2004 | Arima et al. |
| 2004/0182795 A1 | 9/2004 | Dorian et al. |
| 2004/0185544 A9 | 9/2004 | Hei |
| 2004/0209236 A1 | 10/2004 | DePablo et al. |
| 2004/0229205 A1 | 11/2004 | Ericson et al. |
| 2005/0074743 A1 | 4/2005 | Purmal et al. |
| 2005/0233302 A1 | 10/2005 | Hess et al. |
| 2005/0256443 A1 | 11/2005 | Bischof et al. |
| 2006/0177811 A1 | 8/2006 | Sehgel et al. |
| 2007/0031812 A1 | 2/2007 | Holme |
| 2007/0190636 A1 | 8/2007 | Hassanein et al. |
| 2008/0044803 A1 | 2/2008 | Gyonggossy-Issa |
| 2009/0191537 A1 | 7/2009 | Mayaudon |
| 2009/0259162 A1 | 10/2009 | Ohashi et al. |
| 2011/0117647 A1 | 5/2011 | Mayaudon |

FOREIGN PATENT DOCUMENTS

| | | |
|---|---|---|
| DE | 195 19886 A1 | 12/1995 |
| DE | 691 23 569 T2 | 6/1997 |
| DE | 699 12 457 T2 | 8/2004 |
| EP | 0 108 588 B1 | 6/1989 |
| EP | 0 237 863 B1 | 4/1990 |
| EP | 0510 185 B1 | 12/1996 |
| EP | 0 754 461 A2 | 1/1997 |
| EP | 0 853 881 A2 | 7/1998 |
| EP | 0 853 882 A2 | 7/1998 |
| EP | 1 109 447 B1 | 10/2003 |
| EP | 1 435 241 A1 | 7/2004 |
| EP | 1 736 051 A2 | 12/2006 |
| EP | 2077074 A2 | 7/2009 |
| FR | 2 529 787 | 2/1984 |
| FR | 2 663 505 | 12/1991 |
| FR | 2 672 129 | 7/1992 |
| FR | 2 691 911 | 12/1993 |
| FR | 2 782 166 | 2/2000 |
| JP | 8165245 A | 6/1996 |
| WO | WO 87/05468 | 9/1987 |
| WO | WO 92/08349 | 5/1992 |
| WO | WO/09208349 A1 | 5/1992 |
| WO | WO 92/18136 | 10/1992 |
| WO | WO/0416099 A1 | 1/1994 |
| WO | WO/09603139 A | 2/1996 |
| WO | WO 96/13158 | 5/1996 |
| WO | WO 98/56247 | 12/1998 |
| WO | WO 00/11946 | 3/2000 |
| WO | WO 01/45502 | 6/2001 |
| WO | WO 02/23988 | 3/2002 |
| WO | WO 02/43485 | 6/2002 |
| WO | WO 02/087560 | 11/2002 |
| WO | WO 03/000052 | 1/2003 |
| WO | WO 03/049634 | 6/2003 |
| WO | WO 03/049784 | 6/2003 |
| WO | WO 03/090794 | 11/2003 |
| WO | WO 2004/112477 | 12/2004 |
| WO | WO 2005/013689 | 2/2005 |
| WO | WO 2006/012615 | 2/2006 |
| WO | WO 2006/044790 | 4/2006 |
| WO | WO 2006/076401 | 7/2006 |
| WO | WO 2006/088455 | 8/2006 |

(56) References Cited

FOREIGN PATENT DOCUMENTS

| WO | WO 2007/003382 | 1/2007 |
|---|---|---|
| WO | WO 2007/047687 | 4/2007 |
| WO | WO/070647687 A2 | 4/2007 |
| WO | WO/07054160 A2 | 5/2007 |
| WO | WO 2007/067482 | 6/2007 |
| WO | WO/07082916 A1 | 7/2007 |
| WO | WO/0200827917 A2 | 3/2008 |
| WO | WO/08037481 A2 | 4/2008 |
| WO | WO/08048228 A2 | 4/2008 |
| WO | WO 2008/089776 | 7/2008 |
| WO | WO/08113017 A2 | 9/2008 |

OTHER PUBLICATIONS

Murphy, S., et al., "Amino Acid Metabolism During Platelet Storage for Transfusion", British Journal of Haematology, Jan. 1, 1992, pp. 585-590.
Shimizu, T., et al., "Roles of acetate and phosphate in the successful storage of platelet concentrates prepared with an acetate-containing additive solution", Transfusion, vol. 33, No. 4, Jan. 1, 1993, pp. 304-310.
Sweeney, J., et al., "L-Carnitine and Its Possible Role in Red Cell and Platelet Storage", Transfusion Medicine Reviews, vol. 18, No. 1, Jan. 2004, pp. 58-65.
EP Communication dated Apr. 16, 2012 regarding European Search Report and Annex for EP Application No. 08 022161.
Hirayama, J., et al., "Storage of Platelets in 30 percent plasma and 70 percent M-sol additive solution", Transfusion, vol. 48, Mar. 2008 pp. 567-568.
Azuma, H., et al., "Reduction in adverse reactions to platelets by the removal of plasma supernatant and resuspension in a new additive solution", Transfusion, vol. 49, Feb. 2009, pp. 214-218.
Petronilli, et al., Modulation of the Mitochondria cyclosporin—A Sensitive Permeability Transition Pore, 1993, J. Biol. Chem, vol. 208 pp. 1011-1016.
Gulliksson, et al., Storage of Platelets in Additive Solutions, Effects of Phosphate 2000, Vox Sangunis, vol. 78, pp. 176-184.
Siliprandi, et al., Stimuation of Oxidation of Mitochondrial Fatty Acids and Acetate by acetyl carnitine 1965, Biochem J., vol. 96, pp. 777-780.
Hiriyama, et al., Storage of Platelets in a Novel Additive Solution (M-sol) which is Prepared by Mixing Solutions that are not Especially Approved for Platelet Storage, Jun. 2007, Transfusion, vol. 47, pp. 960-965.
Van Rhenen, et al., Therapeutic Efficacy of Pooled Buffy-coat Platelet Components Prepared and Stored With a Platelet Additive Solution, Transfus Med. Aug. 14, 2004(4): 289-95.
Diedrich, et al., In Vitro and in Vivo Effects of Potassium and Magnesium on Storage up to 7 days of Apheresis Platelet Concentrates in Platelet Additive Solution. Vox Sang, Feb. 2008 '94 (2): 96-102. Epub Nov. 22, 2007.
Kerkhoffs, et al., A Muticenter Randomized Study of the Efficacy of Transfusions With Platelets Stored in Platelet Additive Solution II Versus Plasma Blood 108: 3210-3215, published online Jul. 6, 2006.
Vetlesen, et al., Platelet Activation and Residual Activation Potential During Storage of Hyperconcentrated Platelet Products in Two Different Platelet Additive Solutions, Transfusion, Aug. 2005; 45(8): 1349-55.
Sweeney J, et al., Storage of Platelet-rich Plasma-Derived Platelet Concentrate Pools in Plasma and Additive Solution, Transfusion, May 2006; 46(5):835-40.
Holme, et al., Blood Collection and Components, The Expression of P-Selectin During Collection, Processing, and Storage of Platelet Concentrates: Relationship to Loss of In Vivo Viability, Transfusion 1997; 37:12-17.
Holme, et al., A Multi-Laboratory Evaluation of In Vitro Platelet Assays: the Tests for Extent of Shape Change and Response to Hypotonic Shock, Transfusion 1998; 38:31-40.
Bertolini, et al.., A Multicenter Evaluation of Reproducibility of Swirling in Platelet Concentrates, Transfusion, 1994; 34:796-801.
EP Communication with European Search Report for EP Application No. 12 16663 dated Aug. 9, 2012.
Tobian, A., et al,,"Prevention of allergic transfusion reactions to platelets and red blood cells through plasma reduction", Transfusion, vol. 49, pp. 199-201, 2009.
Bertolini, F., et al., "Role of acetate during platelet storage in a synthetic medium", Transfusion, vol. 32, pp. 152-156, 1992.
VandenBroeke, T., et al., "Platelet storage solution effects on the accuracy of laboratory tests for platelet function: a multi-laboratory study", Vox Sanguinis, vol. 86, pp. 183-188, 2004.
Radwanski, K., et al., "Apheresis Platelets Store successfully with 10% Plasma in Reformulated PAS with Bicarbonate" Abstracts from the American Society for Apheresis 31$^{st}$ Annual Mts, May 26-29, 2010, Journal of Clinical Apheresis. vol. 25, pp. 1-2, 2010.
Springer, W. et al., "Evaluation of a New Reagent for Preserving Fresh Blood Samples and Its Potential Usefulness for Internal Quality Controls of Multichannel Hematology Analyzers",American Journal of Clinical Pathology, vol. 111, No. 3, pp. 387-396. Mar. 1, 1999.
Radwanski, K., et al., "Apheresis Platelet Concentrates Can Be Collected in 5% Plasma with 95% PAS-5 and Stored for at Least 7 Days", Transfusion, vol. 50 Supl. 2, S95-40A Abstract Presentations from AABB Annual Meeting Baltimore, MD, Oct. 9-12, 2010.
Radwanski, K., et al., "Storage of Aphersis Platelets with Low Residual Plasma in Reformulation PAS with Bicarbonate", Vox Sanguinis, vol. 99, Supl. 1, P-0347, pp. 220-221 Abstracts of the XXXIst International Congress International Society of Blood, 2010.
Transfusion in joint cooperation with the 43$^{rd}$ Congress of the DGTI, Berlin DE, Jun. 26-Jul. 1, 2010.
International Search Report and Written Opinion dated Jun. 29, 2012, for PCT/US2012/032551.
International Preliminary Report on Patentability dated Oct. 8, 2013, for PCT/US2012/032551.
Adams, G.A., and Rock G. "Storage of human platelet concentrates in an artificial medium without dextrose" Transfusion 28:17 (1988)—Abstract only.
Adams G.A. et al. "Survival and recovery of human platelets stored for five days in a non-pisma medium" Blood 67:672 (1986)—Abstract only.
Holme S et al. "Improved in vivo and in vitro viability of platelet concentrates stored for 7 days in a platelet additive solution" Brit J. Haemotology 66:233 (1987)—Abstract only.
Murphy S. et al. "Platelet storage in synthetic media lacking glucose and bicarbonate" Transfusion 31:16 (1991)—Abstract only.
Extended European Search Report dated Aug. 25, 2014, for EP Application No. 12768563.4.

\* cited by examiner

PRIOR ART

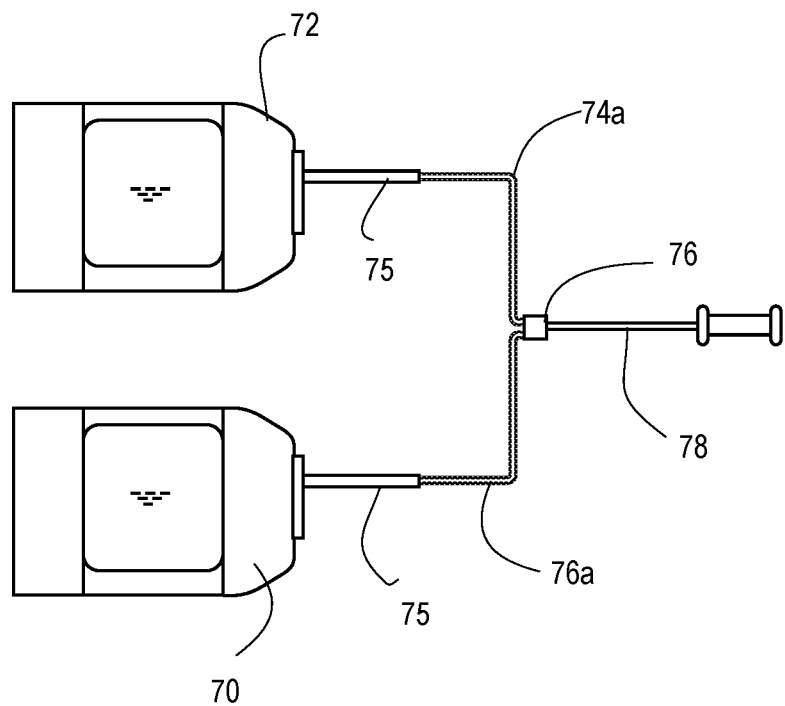

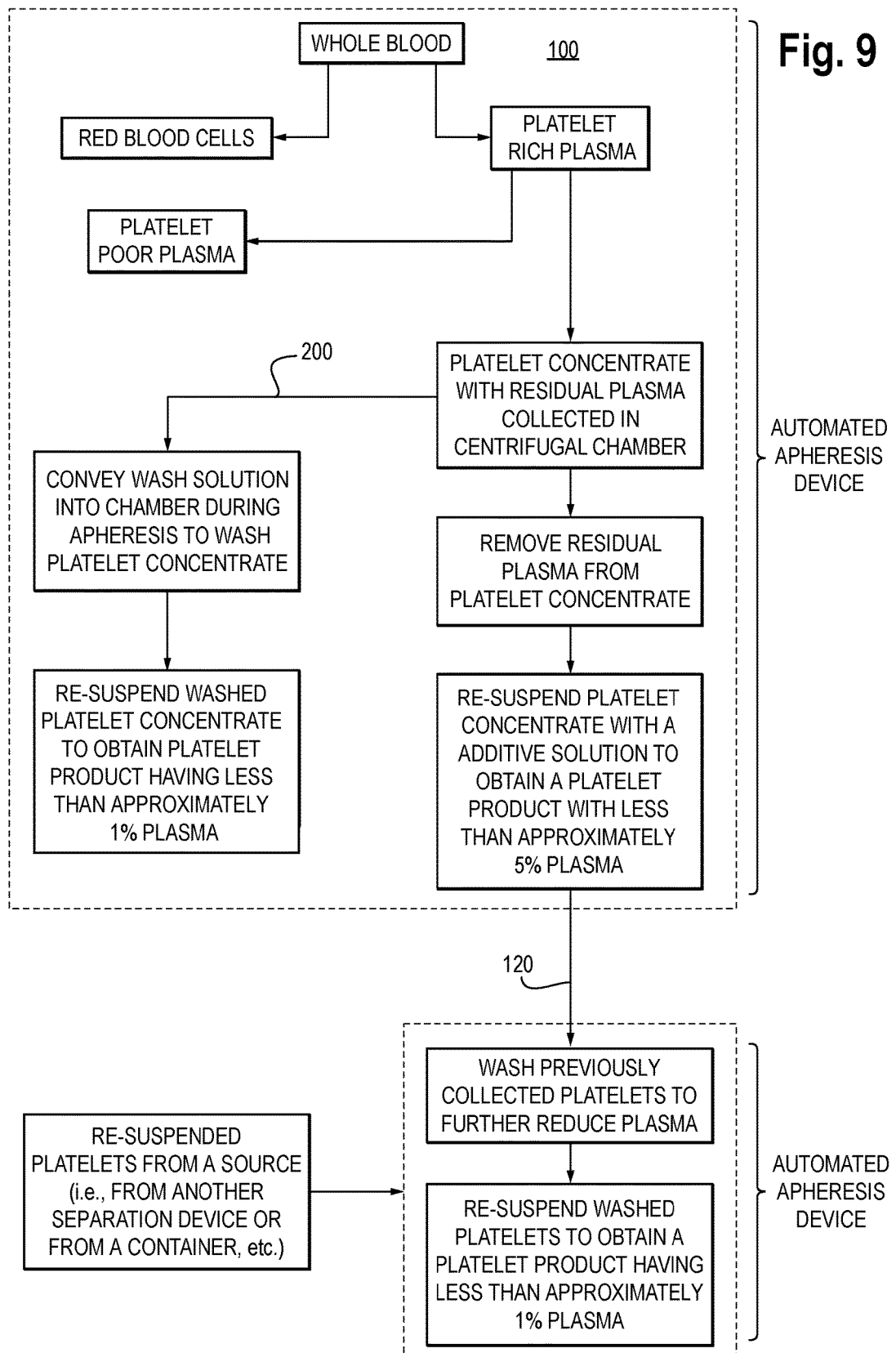

AUTOMATED METHODS AND SYSTEMS FOR WASHING PLATELET CONCENTRATES

CROSS-REFERENCE TO RELATED APPLICATIONS

This application is a divisional of U.S. application Ser. No. 14/110,076, now U.S. Pat. No. 9,402,866, which is a national stage of International Patent Application No. PCT/US2012/032551, filed Apr. 6, 2012, which claims the benefit of U.S. Provisional Patent Application Ser. No. 61/472,952, filed Apr. 7, 2011, and U.S. Provisional Patent Application Ser. No. 61/541,793, filed Sep. 30, 2011, the contents of all of which are incorporated by reference herein in their entireties.

FIELD OF THE DISCLOSURE

The present disclosure relates to storage media for blood components such as blood platelets, which optimize energy metabolism of platelets stored in vitro to preserve and prolong platelet functionality. More particularly, the present disclosure relates to storage media that includes a synthetic storage solution and plasma, where a reduced amount of plasma may be utilized.

The present disclosure also relates to automated systems and methods for processing biological fluid to obtain substantially plasma-reduced platelets. More particularly, the present disclosure relates to systems and methods for reducing the residual plasma volume remaining in platelet concentrate obtained during an apheresis procedure, where the residual plasma volume may be reduced to less than 5% of the total volume of the platelet concentrate. The present disclosure also relates to using automated systems and methods for washing platelet concentrate to reduce the residual plasma volume to 1% or less than 1% of the total volume of the platelet concentrate.

DESCRIPTION OF RELATED ART

Methods of separating platelets from whole blood as well as methods for storing platelets for later transfusion to a patient are well known. Various synthetic media useful for the storage of platelets are disclosed in U.S. Pat. No. 5,569,579 (Murphy) and U.S. Pat. No. 5,908,742 (Lin et al.), which are incorporated herein by reference. The platelets may be stored in a platelet storage medium that includes an aqueous storage solution and some amount of plasma.

U.S. Patent Application Publication US2009/0191537, filed Dec. 18, 2008, the entire contents of which is incorporated herein by reference, discloses synthetic platelet storage media that includes sodium chloride, sodium citrate, sodium acetate, sodium phosphate, glucose, magnesium and/or potassium and other additives.

BACKGROUND

Whole blood is made up of various cellular components such as red cells, white cells and platelets suspended in its liquid component, plasma. Whole blood can be separated into its constituent components (cellular or liquid), and the desired separated component can be administered to a patient in need of that particular component. For example, platelets can be removed from the whole blood of a healthy donor, collected, and later administered to a cancer patient, whose ability to "make" platelets has been compromised by chemotherapy or radiation treatment.

Commonly, platelets are collected by introducing whole blood into a centrifuge chamber wherein the whole blood is separated into its constituent components, including platelets, based on the size and densities of the different components. This requires that the whole blood be passed through a centrifuge after it is withdrawn from, and before it is returned to, the donor. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted cooperatively on the hardware. The centrifuge assembly spins a disposable centrifuge chamber in the fluid processing assembly during a collection procedure, thereby separating the blood into its constituent components.

"On line" automated blood separation systems are today used to collect large numbers of platelets. On line systems perform the separation steps necessary to separate platelets from whole blood in a sequential process with the donor present. On line systems draw whole blood from the donor, separate out the desired platelets from the drawn blood, and return the remaining red blood cells and plasma to the donor, all in a sequential flow loop. Large volumes of whole blood can be processed using an automated on line system. Due to the large processing volumes, large yields of concentrated platelets can be collected. Moreover, since the donor's red blood cells are returned, the donor can donate platelets for on line processing much more frequently.

In the automated, on-line separation and collection of platelets, sometimes referred to as platelet apheresis or simply "plateletpheresis", the platelets are separated from whole blood and concentrated in the centrifuge chamber or elsewhere in the fluid processing set (hereinafter "platelet concentrate" or "PC"). Although most of the plasma is removed during apheresis, a volume of plasma still remains in the PC, hereinafter referred to as "residual plasma". Platelets may also be derived from buffy coats obtained from manually collected units of whole blood. A plurality of buffy coats are typically pooled to provide an amount or dose of platelets suitable for transfusion. The platelets, whether collected by apheresis or from pooled buffy coats, are typically reconstituted in a liquid medium, such as plasma and/or a synthetic storage solution, for storage until needed for transfusion to a patient.

For the stored platelets to be suitable for later administration they must substantially retain their viability and platelet function. A number of interrelated factors may affect platelet viability and function during storage. Some of these factors include the anticoagulant used for blood collection, the method used to prepare the platelets, the type of storage container used, and the medium in which the platelets are stored.

Currently, platelets may be stored for five or even seven days at 22° C. After seven days, however, platelet function may become impaired. In addition to storage time, other storage conditions have been shown to affect platelet metabolism and function including pH, storage temperature, total platelet count, plasma volume, agitation during storage and platelet concentration.

A variety of assays have been developed which attempt to determine the quality of stored platelets and the in vivo viability of those platelets when transfused to a patient. For instance, the percentage of platelets that respond appropriately to an ADP agonist (the ESC assay) and the percentage of platelets that respond appropriately to hypotonic shock (HSR assay) are two assays which are thought to correlate well with viability of stored platelets. ESC is a photometric assessment of discoid platelet shape change in response to an ADP agonist. VandenBroeke, et al., "Platelet storage solution effects on the accuracy of laboratory tests for platelet function: a multi-laboratory study." *Vox Sanguinis* (2004) 86, 183-188.

The results of the HSR (Hypotonic Shock Response) assay are often considered to correlate strongly with the in vivo effectiveness of platelets when they are introduced into an individual. This assay measures the ability of platelets to recover a discoid shape after swelling in response to a hypotonic environment. Higher scores on either the HSR or ESC assay appear to correlate with increased viability of the platelets when transfused to patients. The methods and uses of the HSR and ESC assays are described in more detail by Holme et al. *Transfusion*, January 1998; 38:31-40, which is incorporated by reference herein.

Another assay for measuring platelet viability based on platelet shape is the Morphology Score for the platelets during and after storage. Morphology Scores may be determined by, for example, the Kunicki Method, whereby a selected number of platelets in a sample are examined to determine the shape, e.g., discoid, spherical, dendritic or balloon. The number of each shape is then multiplied by a selected multiplier and the resultant numbers are summed to arrive at a Morphology Score. A score of 250-400 is typically indicative of a viable platelet population.

Another shape based assay is the so called "swirling assay" which has also been used as a measure of the quality of platelet concentrates. The swirling assay is based on the ability of discoid platelets to reflect light, producing a shimmering phenomenon. As described by Bertolini and Murphy, *Transfusion* 1994; 34:796-801 and *Transfusion* 1996: 36:128-132 and incorporated herein by reference, platelet samples scoring positive in a swirling assay are believed to be of higher quality than samples scoring intermediate or negative for swirling.

The presence of the glycoprotein P-selectin on the surface of platelets is also used to characterize the viability of platelets upon transfusion with the presence of P-selectin believed to indicate a loss of viability. As described by Holme et al. *Transfusion* 1997; 37:12-17 and incorporated herein by reference, platelets undergo a shape change transforming from disc shaped to sphere shaped upon platelet activation. This activation is thought to involve the secretion of β-thromboglobulin from the alpha granules resulting in the appearance of P-selectin on the surface of the platelets. Antibodies directed against P-selectin, such as the monoclonal antibody CD62P, are used to detect the presence of P-selectin on the surface of platelets and have been used as a marker of platelet activation and a decreased viability of the platelets upon transfusion.

Another marker of the quality of platelets is extracellular levels of lactate dehydrogenase. Lactate dehydogenase is an intracellular enzyme and therefore higher extracellular levels of lactate dehydogenase are thought to reflect increased levels of platelet lysis.

In order to maintain viability, platelets must generate new adenosine triphosphate (ATP) continuously to meet their energy needs. As shown in FIG. 1 platelets use two metabolic pathways to generate ATP: (a) anaerobic glycolysis followed by lactic acid fermentation or (b) glycolysis followed by oxidative phosphorylation. Glycolysis results in one mole of glucose being converted to 2 moles of pyruvate, and two moles of ATP. The pyruvate can then undergo lactic acid fermentation also called anaerobic glycolysis. Although no additional ATP is produced in lactic acid fermentation, the conversion of pyruvate to lactic acid regenerates $NAD^+$ and allows glycolysis to continue generating at least a small amount of ATP from the metabolism of glucose. Because lactic acid fermentation, which can negatively affect the pH of the medium and platelets stored therein, is stimulated by the absence of oxygen, platelets are typically stored in containers permeable to oxygen to promote oxidative phosphorylation and suppress lactic acid formation.

In oxidative phosphorylation, pyruvate, fatty acid or amino acids are converted to $CO_2$ and water in the citric acid cycle. This pathway requires the presence of an adequate supply of oxygen. Glycolysis followed by oxidative phosphorylation produces 36 moles of ATP per mole of glucose and therefore is much more efficient than glycolysis followed by lactic acid fermentation.

However, rather than utilizing oxidative phosphorylation exclusively, the platelets continue to produce lactic acid through anaerobic glycolysis. Therefore, even in the presence of adequate amounts of oxygen and when stored in media containing glucose, (media such as plasma and certain synthetic storage solutions) the utilization by platelets of glycolysis coupled with lactic acid fermentation for energy production results in the concentration of lactic acid increasing over time. As noted above, the increase in lactic acid gradually acidifies the storage media. This acidification of the media alters platelet physiology and morphology such that when the pH of the media drops below about 6 the platelets may be considered nonviable. Even drops in pH that are too small to render platelets nonviable have been observed to cause decreases in the total amount of ATP. These reductions in ATP affect platelet function as ATP plays a role in platelet adhesion and platelet aggregation. Consequently, it would be desirable to provide a storage medium for platelets that results in the prevention and/or delay of this decrease in pH.

A number of approaches for the storage of platelets for transfusion have been described. Although plasma is effective for storage of platelets, it may not be the ideal medium for platelet storage because plasma itself is a valuable blood component that can be removed from the platelets and then used or further processed for use in the treatment of patients with other disorders.

Another reason for removing some, most, or all of the plasma from platelet concentrate is to prevent allergic transfusion reactions (ATR) to plasma. There may be other reasons for removing at least some or even most of the plasma from the platelets. For example, the presence of certain antibodies in plasma has been correlated with the occurrence of TRALI (transfusion-related acute lung injury) in some patients. Consequently, while residual plasma may be present to some degree in platelets obtained in an apheresis procedure, it may be desirable to reduce the amount of residual plasma in platelets. Preferably, residual plasma may be removed from platelet concentrate in a way that is cost effective, efficient, and which does not affect the in vivo viability of the platelets. Accordingly, it would be desirable to develop automated systems and methods to remove residual plasma from platelets to obtain a platelet concentrate such that upon reconstitution, the platelet product has a substantially reduced volume of plasma such as less than approximately 5% of the total platelet product volume, or even less.

Reductions of residual plasma to below 5% and even to and/or less than 1% plasma may be achieved by "washing" platelets or PC to remove residual plasma. Upon resuspension of washed platelets, the volume of plasma remaining in the resuspended PC may preferably be less than approximately 1% of the total washed platelet product volume. Accordingly, it would be desirable to develop automated systems and methods for washing platelet concentrate to obtain a washed platelet product having less than approximately 1% plasma (and up to approximately 0%).

In place of the removed residual plasma, platelets may be resuspended and stored in some small volume of residual plasma and a substantially greater volume of an alternate storage medium. Synthetic aqueous solutions have been developed to provide a suitable environment for stored platelets, which may be "stand alone" solutions or, as indicated above, used in combination with some amount of plasma. Reducing the amount of residual plasma in platelet concentrate and then combining the plasma-reduced platelet concentrate with a synthetic storage medium may have advantages, such as preserving the in vivo viability of platelets and achieving extended storage times of such platelets. Thus, it would be desirable to combine PC or platelets having a reduced residual plasma volume with synthetic aqueous solutions to obtain a platelet product for storage. InterSol®, a commercially available platelet storage medium is generally described in U.S. Pat. No. 5,908,742 which is incorporated herein in its entirety. InterSol® contains sodium citrate, sodium acetate, sodium phosphate and adjusted to isoosmolarity with sodium chloride. A typical formulation of InterSol® contains 21.5 mM (3.05 g/L) dibasic sodium phosphate anhydrous ($Na_2HPO_4$), 6.7 mM (1.05 g/L) monobasic sodium phosphate ($NaH_2PO_4.2H_2O$), 10.8 mM (3.18 g/L) sodium citrate $2H_2O$, 32.5 mM (4.42 g/L) sodium acetate $3H_2O$, and 77.3 mM (4.52 g/L) sodium chloride. The InterSol® solution is approximately isoosmolar (about 300 mOsm/L) with platelets and plasma, and has a pH of approximately 7.2. In certain applications (such as, but not limited to, inactivation of pathogens in platelets) InterSol® may be used in combination with plasma ratio of InterSol®/plasma ratio approximately 70%/30% to 60%/40%. Phosphate buffer in InterSol® stabilizes the pH of the solution during platelet storage and increases glycolysis.

While InterSol® has worked satisfactorily in the preservation of blood platelets, further improvements to the storage time and in vivo viability of platelets would be desirable. For example, as noted above, it would be desirable to develop a platelet storage media that reduces platelet utilization of lactic acid fermentation and thus slows the drop in pH that typically occurs during platelet storage, thereby increasing viability of stored platelets to seven days or more, up to as many as 15 days, at 22° C. It would also be desirable to develop a synthetic storage media that allows for the storage of platelets in a reduced amount of plasma (such as less than approximately 30%, preferably less than 5%, and even more preferably less than 1%). It would also be desirable to provide a platelet storage media with a lower concentration of phosphate and a sufficient supply of nutrients to substantially meet the energy needs of the platelets during storage while maintaining a pH between about 6.4 and about 7.4. Finally, it would be desirable to provide an automated system that is programmed for and allows for the collection of platelets in a reduced amount of plasma.

SUMMARY

In one aspect, the present disclosure is directed to a synthetic aqueous solution for the storage of platelets that includes from about 45-125 mM of sodium chloride, from about 5-15 mM sodium citrate, from about 20-40 mM sodium acetate, from about 0.05 to about 12 mM of phosphate, from about 0.05 to about 3 mM magnesium ion, from about 0.05 to about 10 mM potassium chloride, from about 5 to about 40 mM of sodium bicarbonate, and from about 0.5 to about 30 mM of glucose.

In another aspect, the present disclosure is directed to a platelet product comprising platelets in an aqueous solution that includes from about 45-125 mM of sodium chloride, from about 5-15 mM sodium citrate, from about 20-40 mM sodium acetate, from about 0.05 to about 12 mM of phosphate, from about 0.05 to about 3 mM magnesium ion, from about 0.05 to about 10 mM potassium chloride, from about 5 to about 40 mM of sodium bicarbonate, from about 0.5 to about 25 mM of glucose, and up to about 10% plasma.

In a further aspect, the present disclosure is directed to a method of storing platelets. The method includes providing concentrated platelets and combining the concentrated platelets with a selected volume of an aqueous solution that includes from about 45-125 mM of sodium chloride, from about 5-15 mM sodium citrate, from about 20-40 mM sodium acetate, from about 0.05 to about 12 mM of phosphate, from about 0.05 to about 3 mM magnesium ion, from about 0.05 to about 10 mM potassium chloride, from about 5 to about 40 mM of sodium bicarbonate, from about 0.5 to about 30 mM of glucose, and also includes up to about 10% plasma.

In a still further aspect, the present disclosure is also directed to an aqueous solution for the processing of platelets including about 69 mM sodium chloride, about 10 mM sodium citrate, about 30 mM sodium acetate, about 9.3 mM sodium phosphate monobasic dihydrate and dibasic sodium phosphate anhydrous, about 1.5 mM magnesium chloride, about 5 mM potassium chloride, about 16.8 mM of glucose (dextrose) and at least about 10 mM sodium bicarbonate, as well as to methods for washing and/or storing platelets with or in such a solution.

In another aspect, the present disclosure is directed to an automated method for providing substantially plasma-reduced platelets. The method comprises the steps of providing an automated apheresis separator comprising a platelet concentration chamber and concentrating platelets in the chamber, wherein the platelet concentrate comprises platelets suspended in a volume of plasma. The method further comprises the steps of removing a selected volume of plasma from the platelet concentrate and reconstituting the platelet concentrate with an additive solution to obtain a platelet product comprising platelets, aqueous additive solution and plasma, wherein the volume of plasma in said platelet product is 5% or less of the total platelet product volume.

In another aspect, the method may further comprise introducing the platelet product into an automated apheresis separator and removing substantially all of the plasma component from the platelet product, to obtain a second platelet concentrate suspended in a residual volume of plasma. Wash solution may be introduced into the separator to displace substantially all of the residual plasma remaining in the second platelet concentrate and residual plasma may be removed from the separator to obtain a washed platelet concentrate. The method may further comprise the step of reconstituting the washed platelet concentrate in the wash solution to obtain a washed platelet product comprising platelets, wash solution and plasma, wherein the volume of plasma in the product is 1% or less of the total washed platelet product.

In another aspect, the present disclosure is directed to an automated method of washing platelets comprising the steps of providing an automated separation device comprising a platelet concentration chamber, introducing a blood product into the separation device and separating the blood product to obtain a platelet concentrate. The platelet concentrate comprises platelets suspended in a residual volume of plasma. The method further comprises introducing a wash solution into the separation device to displace the residual plasma and removing the residual plasma from the chamber to create a washed platelet product comprising platelets, wash solution and plasma, wherein the volume of plasma in said washed platelet product is 1% or less of the total washed platelet product.

In yet another aspect, the present disclosure is directed to an automated system for processing biological fluid to obtain substantially plasma-reduced platelets. The system comprises a disposable fluid circuit comprising a separation chamber for separating biological fluid into one or more components including platelets suspended in a volume of plasma, a source of aqueous additive solution in openable flow communication with the separation chamber, a separation device adapted to receive the separation chamber for effecting separation of biological fluid and a programmable controller. The controller is programmed to collect platelets suspended in a volume of plasma in the separation chamber, remove substantially all of the plasma from the platelets to obtain a platelet concentrate, introduce additive solution from the additive source into the chamber to reconstitute the platelet concentrate to obtain a platelet product comprising platelets, aqueous additive solution and plasma, wherein the volume of plasma in said platelet product is 5% or less of the total platelet product volume.

In a further aspect, the present disclosure is also directed to a method of washing platelets, including providing an apheresis device, separating platelets suspended in plasma in the apheresis device to obtain concentrated platelets suspended in a selected volume of plasma. The method further includes collecting substantially all of the concentrated platelet suspension, removing any residual plasma remaining in the apheresis device and resuspending the concentrated platelets in a volume of additive solution that includes from about 45-125 mM of sodium chloride, from about 5-15 mM sodium citrate, from about 20-40 mM sodium acetate, from about 0.05 to about 12 mM of phosphate, from about 0.05 to about 3 mM magnesium ion, from about 0.05 to about 10 mM potassium chloride, from about 5 to about 40 mM of sodium bicarbonate, and from about 0.5 to about 30 mM of glucose. The method further includes conveying the resuspended platelets into an apheresis device to remove additional plasma from the platelet suspension to provide a concentrated platelet product that includes platelets and the aqueous additive solution and plasma wherein the volume of plasma is 5% or less of the total platelet product volume.

BRIEF DESCRIPTION OF THE DRAWINGS

FIG. 2A is an example of an alternative container system for mixing the components (compartments) of the synthetic storage solution described herein;

FIG. 9 is a flow-chart diagram showing the various steps in the methods for processing platelets in accordance with the present disclosure.

DESCRIPTION OF THE ILLUSTRATED EMBODIMENTS

Figure 1:
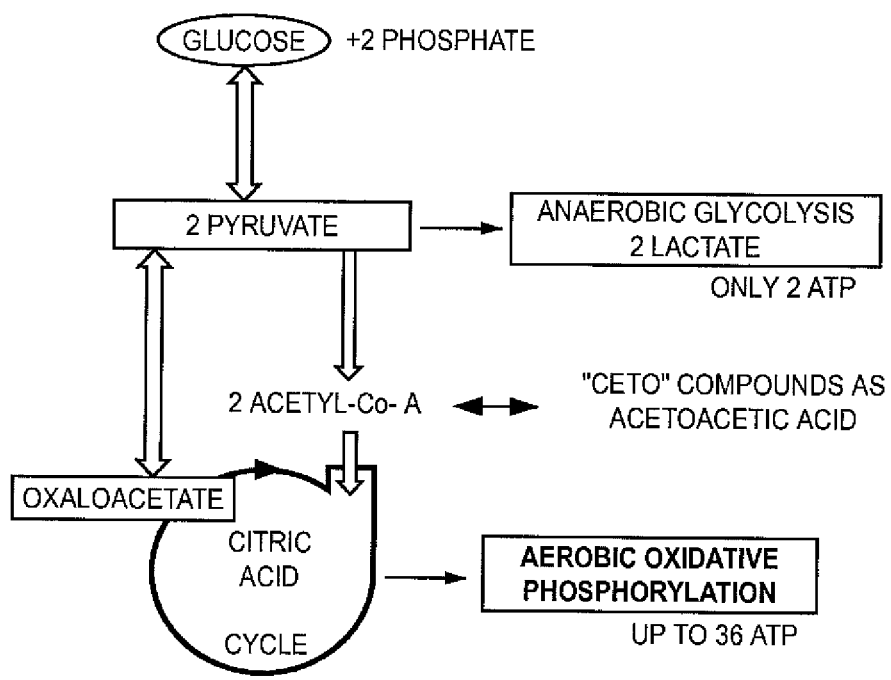
FIG. 1 is a representation of the glycolic and oxidative phosphorylation pathways for ATP production.

The embodiments disclosed herein provide a general description of automated systems and methods for processing blood components, such as platelet concentrate, to remove residual plasma. Automated systems and methods for washing platelet concentrate are also the subject of this disclosure, as are the solutions used in the methods of processing, washing and storing. The embodiments disclosed herein also provide a general description of the storage media and methods for storing blood components, such as platelets. These embodiments are only exemplary, and may be embodied in various forms. Therefore, specific details disclosed herein are not to be interpreted as limiting the subject matter of the invention which is set forth in the accompanying claims.

The platelet storage media described herein include at least an aqueous solution and, typically, some amount of plasma. Platelet products described herein include the platelet storage media (platelet storage solution and plasma) and the platelets stored therein. Preferably the amount of plasma that makes up the platelet storage media is "reduced". For example, less than about 40% of plasma may be utilized, more preferably less than about 20%, and between about 10%-20%. More preferably, however, the volume of plasma is even less than 10%, such as 5% or less and between 0% and 5%.

It is presently believed and understood that platelet storage media described herein promote ATP production through the oxidative phosphorylation pathway over ATP production through anaerobic glycolysis, thereby limiting lactic acid formation and consequently, a decrease in the pH of the medium. Accordingly, platelets stored in the platelet storage media described herein exhibit properties such as response to hypotonic shock, levels of P-selectin, morphology, etc., that are typically at least as good or better than platelets stored in plasma or other storage media.

In one embodiment, a platelet storage medium is provided that includes a synthetic aqueous storage solution that itself includes one or more nutrients and buffer(s) in a salt solution. The buffer(s), one of which may be a phosphate buffer may include a lower concentration (as compared to InterSol® or other storage solution or media) of phosphate in the platelet storage medium. Additional buffering may be provided by a selected concentration of bicarbonate ion. Bicarbonate may be provided as sodium bicarbonate.

Thus, an embodiment of the synthetic aqueous storage solution described herein may include 45-125 mM sodium chloride, 5-15 mM sodium citrate, 20-40 mM sodium acetate, 0.5-12 mM phosphate buffer, 0.05-3 mM magnesium ion, and 0.5-30 mM glucose, with the initial pH of the complete storage media ranging from 6.8-7.3. The aqueous storage solution may further include 5-40 mM of sodium bicarbonate. Optionally, 0.05-3 mM calcium chloride and/or 0.05-10 mM potassium chloride may also be present in synthetic platelet storage solution.

In a more specific embodiment the sodium chloride may be present from about 50 mM to about 110 mM. More particularly, the sodium chloride may be present from about 58 mM to about 90 mM, or from about 65 mM to about 80 mM. In one embodiment, the concentration of sodium chloride in the final (combined) aqueous solution may be about 69 mM.

Also, more preferably, the sodium citrate may be present from about 7 mM to about 13 mM, and more typically from about 9 mM to about 12 mM. In one embodiment, the concentration of sodium citrate in the final (combined) aqueous solution may be about 10 mM.

As set forth above, the storage solution may also include an amount of sodium acetate. In one embodiment the sodium acetate may be present from about 24 mM to about 36 mM, and more preferably from about 28 mM to about 33 mM. In one embodiment, the final concentration of sodium acetate in the final (combined) aqueous solution may be about 30 mM.

As noted above, additional buffering may be provided by bicarbonate ion. Bicarbonate may preferably be provided as the sodium salt, sodium bicarbonate $NaHCO_3$. Sodium bicarbonate may be present in the synthetic solution in an amount of between approximately 5 mM-40 mM, and more preferably between approximately 8 mM-25 mM. In one embodiment, the final concentration of bicarbonate in the final (combined) solution may be at least about 10 mM. In another embodiment, the concentration of bicarbonate may be about 20 mM.

Preferably, a buffer such as phosphate is also included in the storage solution described herein. In one embodiment, phosphate may be present from about 0.5-12 mM, 3 mM to about 11 mM, and more typically from about 6 mM to about 10 mM. Examples of sources of phosphate include (but are not limited to) sodium phosphate and/or potassium phosphate. In addition, the sodium phosphate and potassium phosphate used may include various forms of phosphate such as either or both monobasic and dibasic forms of phosphate. For example, a phosphate buffer having a phosphate concentration of 9.4 mM may contain approximately 7.2 mM (1.017 g/L) dibasic sodium phosphate anhydrous ($Na_2HPO_4$) and 2.2 (0.350 g/L) mM monobasic sodium phosphate dihydrate ($NaH_2PO_4.2H_2O$).

It is understood that the conversion of 1 mole of glucose to 2 moles of pyruvate requires two (2) moles of inorganic phosphate. Consequently, the metabolism of glucose to pyruvate, the step preceding oxidative phosphorylation, requires the presence of phosphate. However, high levels of phosphate may alter the permeability of the mitochondrial membrane and reduce the likelihood of maintaining intact platelet mitochondria. As the citric acid cycle of oxidative phosphorylation takes place in the mitochondria, it is desirable to maintain intact mitochondria to optimize platelet utilization of oxidative phosphorylation during storage in order to maintain a stable pH in the medium and adequate levels of ATP in the platelets.

In platelets stored in plasma, oxidative phosphorylation is active and the mean lactic acid concentration is about 18 mEq/L. Therefore, a synthetic storage medium which has a phosphate concentration of less than approximately 10 mM and promotes oxidative phosphorylation during platelet storage should be capable of buffering the $H^+$ produced from the fraction of pyruvate produced by glycolysis that undergoes lactic acid fermentation. Consequently, the phosphate concentration of the synthetic storage solution described herein is preferably below 10 mM in order to maintain intact platelet mitochondria with normal membrane permeability. For example, the addition of 300 ml of an aqueous solution with a phosphate concentration of about 9.4 mM is combined with a platelet concentrate in plasma to produce a suspension of platelets in a storage solution comprising 10% plasma, the final phosphate concentration will be approximately 15 mEq/L.

The storage solution disclosed herein may also be buffered by amino acids. The amino acids may be used as the primary buffering agents, or may be used in conjunction with other buffering agents such as phosphate. In one embodiment the amino acid, histidine may be used to buffer the storage solution. Thus, the storage solution may contain amino acids from about 1 mM to about 7 mM, or from about 2 mM to about 5 mM. More particularly, the storage solution may contain histidine from about 1 mM to about 7 mM, or from about 2 mM to about 5 mM.

The storage solution described herein may also include a selected concentration of magnesium ion. In one embodiment, magnesium ion may be present in the synthetic solution at concentrations close to plasma levels which will be about 3 mEq/L (1.5 mM). Magnesium ion at high cytosolic (intercellular) concentrations appears to play a role in resealing of the mitochondria [Petrollini V, Cola C, Bernardi P, Modulation of the mitochondria cyclosporin A-sensitive permeability transition pore, *J. Biol. Chem.* 1993; 268; 1011-6]. Consequently, magnesium ion in the medium should maintain the optimal intercellular magnesium levels in the platelets and may promote oxidative phosphorylation in the platelets and in so doing help maintain the pH of the medium. Preferably, magnesium ion may be added either as a chloride or a sulfate salt. In one embodiment magnesium ion may be present from about 0.05 mM to about 4 mM. More typically, magnesium ion may be present from about 0.1 mM to about 3.5 mM, or from about 0.5 mM to about 3.0 mM, or from about 1.0 mM to about 2.5 mM. In one particular embodiment, magnesium ion may be present from about 1.4 mM to about 2.2 mM. In one embodiment, the concentration of magnesium (chloride) in the final (combined) aqueous solution may be about 1.5 mM.

The storage solution described herein may also include a selected concentration of calcium ion. For example, calcium ion may be present in the aqueous solution. The presence of calcium ion in the medium may assist in maintaining intracellular magnesium ions. Stress can cause an influx of calcium into platelets, therefore to maintain free calcium in the complete storage medium, the synthetic storage media may initially contain about 0.5 mM to about 2.5 mM (1 to 5 mEq/) calcium ion. In one embodiment calcium ion may be present from about 0.05 mM to about 3 mM. More particularly, calcium ion may be present from about 0.4 mM to about 2.8 mM, or from about 0.6 mM to about 2.2 mM, or about 0.8 mM to about 1.2 mM.

The storage solution described herein may also include a selected concentration of potassium ion (from, for example, potassium chloride). The presence of potassium ion in the medium may assist in maintaining intracellular magnesium ion concentration. Potassium ion also appears to be involved in the transport of pyruvate across the mitochondria membrane for oxidative phosphorylation in the citric acid cycle (TCA cycle).

Preferably, potassium ion may be present from about 1 mM to about 10 mM. More preferably, potassium ion may be present from about 2 mM to about 9 mM, or from about 3 mM to about 8 mM, or from about 4 mM to about 7 mM, or from about 4.5 mM to about 6.5 mM. In one embodiment, the concentration of potassium (chloride) in the final (combined) aqueous solution may be about 5 mM.

The storage solution described herein may include a combination of magnesium ion, calcium ion, and potassium ion, or any other subcombinations of these three ions may be present in the storage solution. Where the storage solution is separated into two compartments (described in detail below), such as a neutral buffered physiological compartment and a carbohydrate compartment, as shown, for example in FIG. 2, one or more of the magnesium ion, calcium ion, and potassium ion may be contained in either or both compartments.

In the storage solution and storage media described herein, a carbohydrate is preferably included as a nutrient source of intermediate metabolites for production of energy. Glucose and other carbohydrates such as sucrose are nutrients for the platelets and can provide an important source of energy for platelets in storage by being the primary source of intermediate metabolites for the production of energy in the citric acid cycle. However, it may be important to regulate the concentration carbohydrates in the storage medium, because an excess concentration of a carbohydrate such as glucose appears to cause increased lactic acid production. In one embodiment, the initial glucose concentration may be from about 0.5 mM to about 30 mM. More preferably, the initial glucose concentration may be from about 2 mM to about 22 mM. In some embodiments the initial glucose concentration may be from about 4 mM to about 20 mM. Preferably, the initial glucose concentration may be from about 6 mM to about 19 mM. In other embodiments the initial glucose concentration may be from about 10 mM to about 18 mM. In one embodiment, the concentration of glucose in the final (combined) aqueous solution may be about 16.8 mM. Carbohydrates such as sucrose can be used either in place of glucose or in combination with glucose as primary energy sources.

Figure 2:
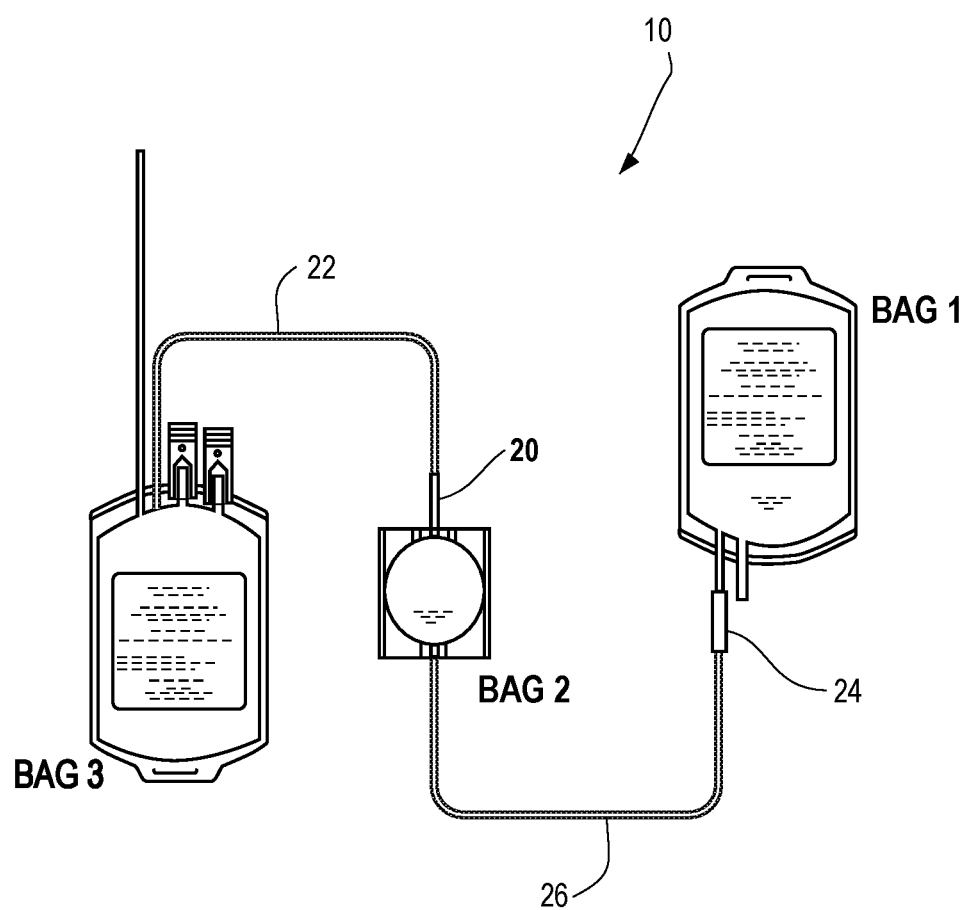
FIG. 2 is an example of a container system for mixing the components (compartments) of the synthetic storage solution.

As noted above, the carbohydrate, for instance glucose, may be stored in a concentrated solution separately from the neutral buffered physiological salts. As shown in FIG. 2, the concentrated carbohydrate solution may also contain other salts such as the calcium, magnesium, potassium, or sodium salts or any possible subcombination of these salts to raise the osmolarity of the concentrated carbohydrate compartment such that it is close to that of the buffered physiological compartment (Bag 1). To allow heat sterilization, such as autoclaving of the glucose solution, the glucose solution should be acidic for example with a pH between from about 4 to about 6.

As an example of a concentrated carbohydrate solution, 25 ml of the concentrated glucose solution may be combined with 275 ml of the buffered salt solution to produce 300 ml of aqueous solution. In this example, the concentrated glucose solution is 40 g/l glucose which results in a concentration of 3.3 g/L or 0.32% weight/weight glucose in the final platelet mixture.

Carbohydrate such as glucose, and more particularly D-glucose (dextrose) may be added to the platelet storage medium on the processing day (day 1) and/or later during storage, for instance on day 3 or 4 of storage. Addition of carbohydrate subsequent to the processing day may allow lower initial concentrations of carbohydrate to be used in the storage buffer, and as the carbohydrate is metabolized during storage, additional carbohydrate may be added. In this manner, lower concentrations of the carbohydrates are present in the storage medium throughout platelet storage, which as discussed herein, helps to suppress the production of lactic acid.

Thus, in one embodiment, the aqueous synthetic solution referred to herein as PAS-5, or PAS V, includes:

TABLE 1

| Composition (g/L) | PAS-5 |
| --- | --- |
| $Na_3Citrate \cdot 2H_2O$ | 2.94 |
| $Na\ Acetate \cdot 3H_2O$ | 4.08 |
| $NaH_2PO_4 \cdot 2H_2O$ | 0.35 |
| $NaH_2PO_4$ | 1.02 |
| NaCl | 4.06 |
| KCl | 0.37 |
| $MgCl_2$ | 0.30 |
| Glucose | 3.33 |
| $CaCl_2$ | 0.15 |
| Na Bicarbonate | 0.75-1.70 |

Other nutrients may be substituted for or included with the glucose of the synthetic storage solution or storage media. For example, oxaloacetate may be present in the synthetic media or may be added to platelet suspension after the synthetic media has been added to a platelet rich fraction. To further reduce the risk of lactic acid build up during the storage of platelets, the synthetic storage media may be formulated such that it contains no or reduced amounts of glucose and similar carbohydrates, which generate pyruvate through glycolysis. In the absence of these carbohydrates pyruvate is not produced and consequently lactic acid is not produced. To maintain platelet ATP production in the absence of glucose or a similar carbohydrate, oxaloacetate may be added directly to synthetic storage media. Oxaloacetate is a four-carbon molecule found in the mitochondria that condenses with Acetyl Co-A to form the first reaction of the TCA cycle (citric acid cycle). As shown in FIG. 1, in the presence of glucose the oxaloacetate is produced from the oxidation of pyruvate. In the absence of glucose, the oxaloacetate cannot be produced from acetate as the conversion of pyruvate into acetic acid is irreversible. Consequently in the absence of glucose, oxaloacetate may be supplied to the stored platelets either directly or in the form of precursor amino acids such as aspartate.

The presence of oxaloacetate in the medium may allow the metabolism of acetyl Co-A and acetate to generate ATP. The presence of oxaloacetate therefore prevents the accumulation of acetate and the generation of "cetonic" compounds such as acetoacetic acid which can acidify the medium. As oxaloacetate is regenerated during each cycle of oxidative phosphorylation, the storage medium may contain approximately equimolar amounts of oxaloacetate and acetate. In some embodiments oxaloacetate may be present in the synthetic solution from about 10 mM to about 45 mM. More particularly, oxaloacetate may be present in the synthetic solution from about 20 mM to about 40 mM, or from about 24 mM to about 36 mM, or from about 28 mM to about 33 mM.

The storage solution and storage media generally disclosed herein may also include other components that promote oxidative phosphorylation. For example a naturally occurring ester of L-carnitine such as acetyl-L-carnitine may be included in the storage solution. Acetyl-L-carnitine in catalytic amounts has been shown to restore oxidative phosphorylation in aged mitochondria. Therefore, to preserve the mitochondria of stored platelets and promote oxidative phosphorylation of carbohydrates, naturally occurring esters of L-carnitine such as acetyl-L-carnitine may be present in the storage solution. The ester of L-carnitine may be present in the synthetic solution and/or may be added to the platelet suspension after the synthetic solution has been added to a platelet rich fraction. In still other, more specific embodiments, a naturally occurring esters of L-carnitine may be present in the storage solution from about 0.1 µM to about 10 µM. In some embodiments a naturally occurring esters of L-carnitine may be present in the storage solution from about 0.2 µM to about 8 µM. In some embodiments a naturally occurring ester(s) of L-carnitine may be present in the storage solution from about 0.5 µM to about 1.5 µM.

In addition to or as an alternative to the foregoing, the storage medium disclosed herein may further include other components that promote oxidative phosphorylation. An antioxidant may be added to the platelet storage medium or the composition that includes platelets and a storage medium. Examples of antioxidants include glutathione, selenium and the like. In some embodiments the antioxidant may be present in the synthetic solution from about 0.5 µM to about 3 mM. More particularly, the antioxidant may be present in the solution from about 1.0 µM to about 2 mM. In some embodiments glutathione, or its precursor N-acetylcysteine, and/or selenium alone or in combination may be present in the synthetic solution from about 0.5 µM to about 3 mM. More particularly, glutathione, or its precursor N-acetylcysteine, and/or selenium alone or in combination may be present in the synthetic solution from about 1.0 µM to about 2 mM. The antioxidants described herein may be included or added to the storage solutions and platelet storage media described herein as well as to known storage solutions such as Intersol® and media that include Intersol®.

To further promote oxidative phosphorylation, the synthetic storage medium or platelets in a storage medium disclosed herein may include other components that may stabilize membranes. For example, a phospholipid or a mixture or phospholipids may be included in the storage solution. In some embodiments, phospholipids may be present in the storage solution from about 0.1 mg/ml to about 7.5 mg/ml, and more typically from about 0.25 mg/ml to about 5 mg/ml. More particularly, L-alpha phosphatidylcholine may be present in the storage solution from about 0.1 mg/ml to about 7.5 mg/ml, and more typically from about 0.25 mg/ml to about 5 mg/ml.

Oxidative phosphorylation may also be promoted by including non-essential amino acids in the synthetic storage medium. For example, non-essential amino acids from about 0.5 mM to about 14 mM may be present in the storage solution, or about 1.0 mM to about 10 mM. More particularly, L-alanine from about 0.5 mM to about 14 mM may be present in the storage solution, or from about 1.0 mM to about 10 Mm.

The synthetic storage solution may also contain unsaturated free long chain fatty acids to promote oxidative phosphorylation. The storage solution described herein may contain from about 0.05 mM to about 1.5 mM of contain unsaturated free long chain fatty acids, or about 0.1 mM to about 1 mM. More particularly the storage medium may contain palmitic acid from about 0.05 mM to about 1.5 mM, or about 0.1 mM to about 1 mM.

As noted above, the storage solutions described above may be used as a "stand-alone" storage medium substantially free of plasma. However, more preferably, the platelet storage medium described herein may also include a selected concentration of plasma. The percentage of plasma is calculated by the equation: $X/(X+Y)\cdot 100\%$=Percentage of Plasma X represents the starting volume of the platelet fraction (platelets in plasma) before resuspension and Y represents the volume of synthetic media (e.g., solution) added to the platelet fraction. If a higher percentage of plasma is desired it may be added to either the starting platelet fraction, the synthetic medium, or the final resuspended platelets and a similar calculation may be used to calculate the percentage plasma. For instance, if $X_1$ is the volume of the platelet fraction (platelets in plasma) and $X_2$ is the volume of added plasma, the total percentage of plasma is calculated with the equation: $(X_1+X_2)/(X_1+X_2+Y)\cdot 100\%$=Percentage of Plasma.

The plasma may be supplied by the residual plasma contained in the platelet rich fractions which are resuspended with storage medium. In addition, and if necessary, plasma may also be added to the storage medium. Thus, if five fractions of buffy coat platelets (platelets in plasma) each having a volume of about 15 ml are pooled and combined with 300 ml of synthetic medium then the percentage of plasma in the suspension ready for storage is calculated $(5\times 15)/[(5\times 15)+300]\cdot 100\%=20\%$. Similarly, if five fractions of buffy coat platelets (platelets in plasma) each having a volume of about seven (7) ml are pooled and combined with 300 ml of synthetic medium then the percentage of plasma in the suspension ready for storage is calculated $(5\times 7)/[(5\times 7)+300]\cdot 100\%=10.4\%$.

Figure 3:
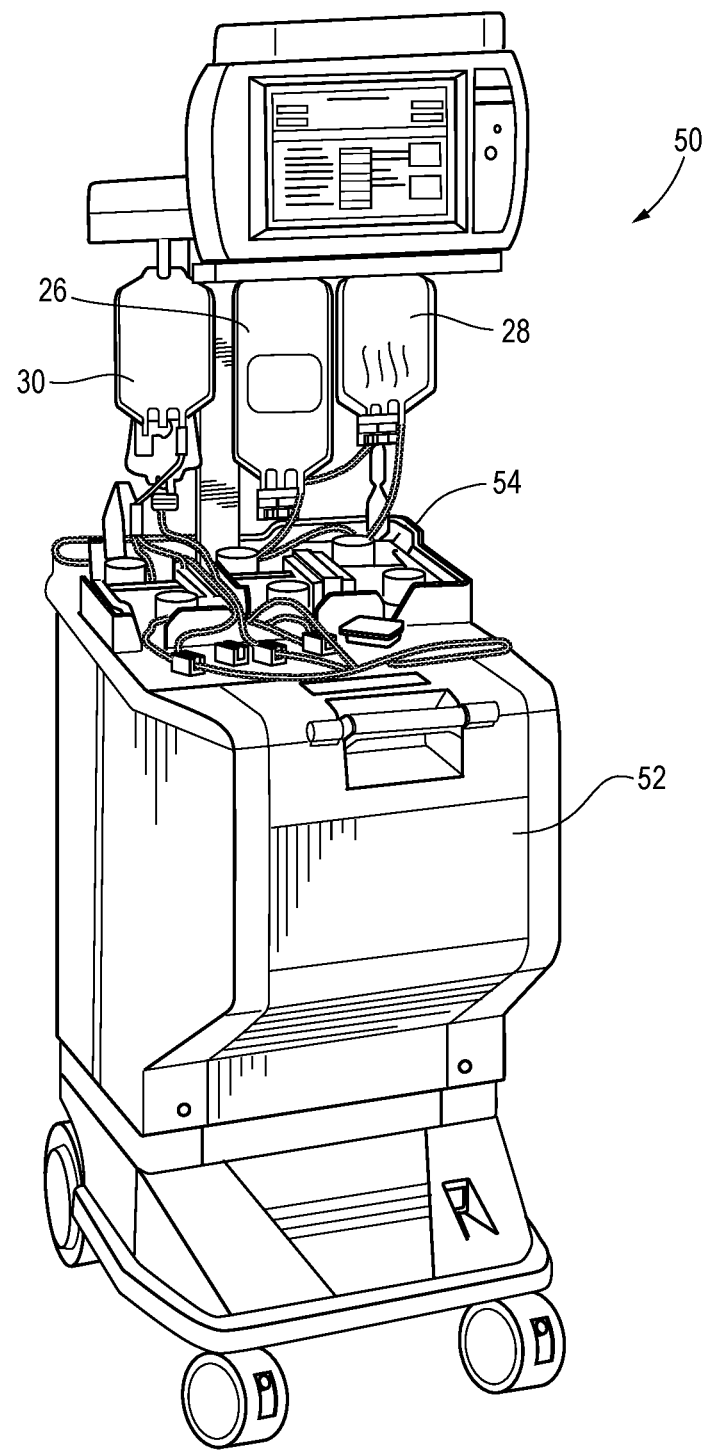
FIG. 3 is a perspective view of an automated apheresis device that may be used in the collection and other processing steps of platelets in accordance with the present disclosure.
Figure 4:
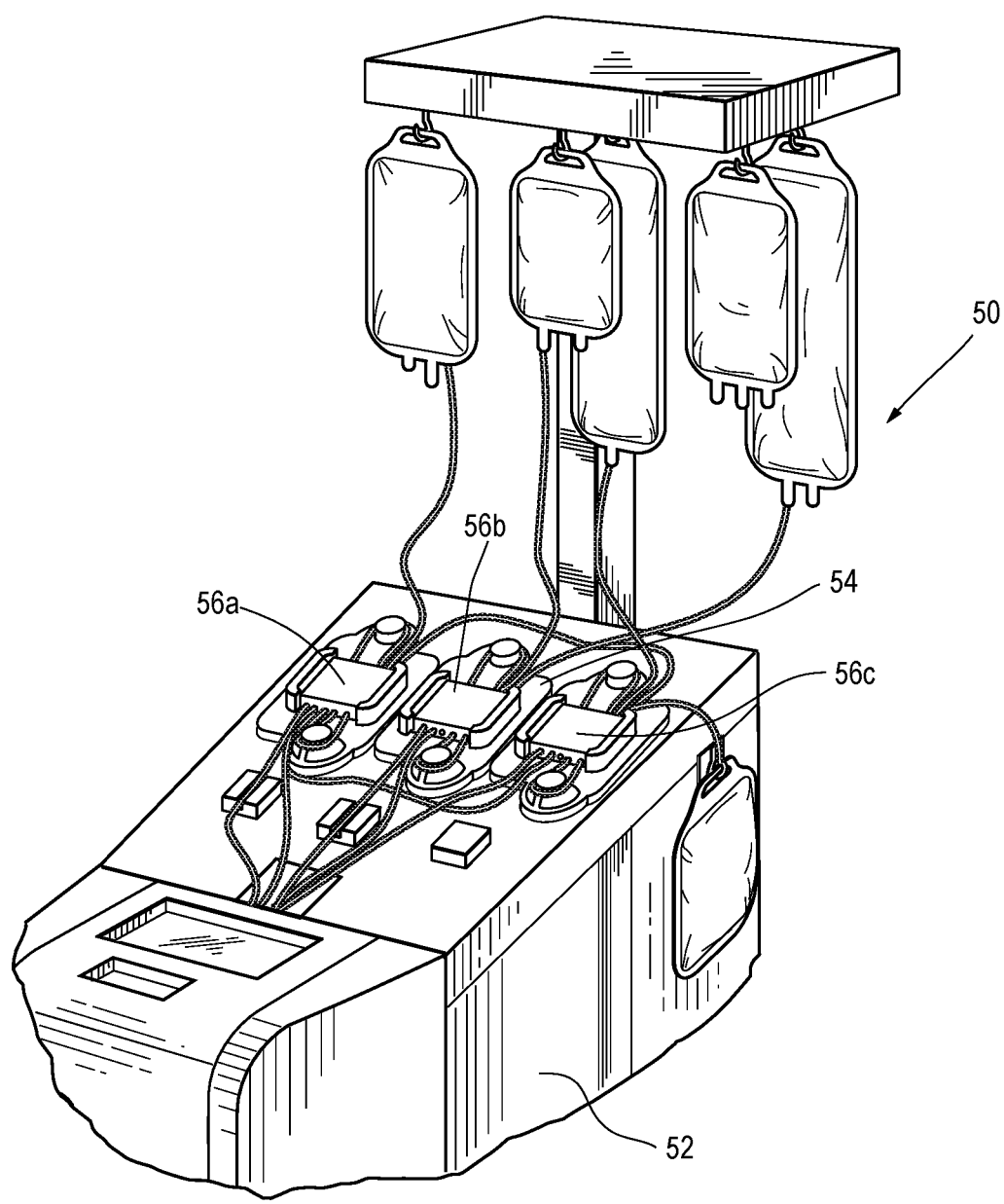
FIG. 4 is an enlarged perspective view of the front panel of the device of FIG. 3 with an exemplary disposable processing set for collecting platelets mounted on the device.

Platelets for storage in the above-identified synthetic medium may, as described above, be obtained from pooled buffy coats, or by other manual and automated methods. For example, platelets may be collected by known automated apheresis devices, such as the Amicus® Separator, available from Fenwal, Inc., of Lake Zurich, Ill. FIGS. 3 and 4 show a representative separation device useful in the separation and collection of platelets and the delivery of the additive solution described herein. The separator 50 includes a hardware component 52 and a disposable processing kit 54 mounted thereon. In one embodiment, the separation principle used by the separator is based on centrifugation, but an automated separator based on a different separation principle may also be used.

With respect to the device shown in FIGS. 3 and 4, a rotating centrifuge is housed within hardware component 52. Disposable kit 54 includes the plastic containers for holding fluid, and may include the additive solution and tubing defining flow paths for movement of the blood, blood components and other fluids through the fluid circuit of kit 54. Disposable processing kit 54 includes one or more cassettes 56 (i.e., cassettes 56a, 56b and 56c shown in FIG. 4) which interface with the front panel of hardware component 52. Cassettes 56a, 56b and 56c include flow paths and valve stations. A series of pneumatically or electrically operated valves (numbered 1-10 in FIG. 5, for example) under the control of a pre-programmed controller of hardware component 52 selectively allow and restrict flow through the flow paths of the cassette and ultimately through the tubing of disposable kit 54. Disposable kit 54 further includes a processing chamber shown generally at 57 of FIG. 5 (which is mounted on a rotor/spool of the centrifuge). Processing chamber 57 has a sub-chamber 58 wherein blood or blood components are separated under the influence of centrifugal force (i.e., the "separation chamber") and a sub-chamber 59 where blood components from sub-chamber 58 can be further processed, separated and/or collected (i.e., the "concentration chamber"). Details of an automated separator suitable for use with the systems and methods described herein are set forth in U.S. Pat. Nos. 5,427,509; 6,312,607; 6,582,349 and U.S. Patent Application Publication 2009/0211987, the entire contents of all of which are incorporated herein by reference. Examples of other automated systems that may be useful in such separation, reconstitution and optional washing procedures are described in U.S. Pat. No. 5,676,644, which is also incorporated by reference herein.

Regardless of the method used to collect the platelets, the relative amount of plasma that may be present in the storage medium described herein will preferably be less than about 20%. More preferably, plasma may be present from about 10% to about 20%.

Further reductions in plasma concentration may also be possible and, indeed, preferred. In one embodiment, the storage medium for the platelets may be plasma-free (i.e., 0% plasma). In other embodiments, plasma may be present in the storage medium (i.e., platelets, plasma and the synthetic aqueous storage solution) in an amount of less than 10%, such as, from about 0.5% to about 10%, or from about 1% to about 9%. In other embodiments plasma may be present in the storage medium from about 2% to about 8%, or from about 3% to about 7%, or from about 4% to about 6%, such as about 5%.

The storage media allows the stored platelets to preserve functionality and viability upon transfusion to a patient for between about 2 to about 15 days, or between about 4 to about 14 days, or between about 5 to about 10 days. Typically, the storage media allows the stored platelets to preserve functionality and viability upon transfusion to a patient for more than about 5 days, or for more than about 7-8 days, including up to nine (9) days and, in some cases, up to 14 days, as determined by at least some of the markers and assays identified above.

Storage medium disclosed herein may be also used in conjunction with methods of photodecontamination of platelets as described, for example, in U.S. Pat. No. 5,908,742 which is herein incorporated by reference in its entirety.

By way of example, but not limitation, illustrations of methods of collecting and storing platelets using the storage media described herein are provided below.

EXAMPLE 1

Preparation of Synthetic Storage Solution

In one embodiment, the partitioning of the ingredients of the synthetic storage solution may consist of 2 parts—part 1, a neutral buffered physiological compartment containing one set of components such as the citrate, acetate, phosphate, sodium ion and optionally magnesium ion, calcium ion, potassium ion, bicarbonate ion, and part 2, an acidic carbohydrate compartment containing the dextrose, and optionally calcium ion, magnesium ion and potassium ion with both compartments having similar osmolarity. In Table 2 an example of a synthetic media with two compartments is presented. The concentrations and/or amounts of the components are as previously described.

TABLE 2

Composition of platelet storage solution in a three bag assembly (in q/Liter)

Buffered Physiological Compartment
Bag 1 containing (in g/L) 275 ml

| | |
|---|---|
| $Na_3$ Citrate•$2H_2O$ | |
| Na Acetate $3H_2O$ | |
| $NaH_2PO_4$•$2H_2O$ | |
| $Na_2HPO_4$ | |
| KCl | |
| NaCl | |
| $NaHCO_3$ | |
| pH | 7.0-7.4 |
| Osmolarity | 300 mOsm/L |

Bag 2 containing (in g/L) 25 ml

| | |
|---|---|
| Carbohydrate Compartment | |
| Dextrose Monohydrate | |
| $CaCl_2$•$2H_2O$ | |
| $MgCl_2$•$6H_2O$ | |
| pH | 4-6 |
| Osmolarity | 292 or 328 mOsm/L |

Bag 3: final storage container (e.g., PL146)

Bicarbonate, such as sodium bicarbonate may be added directly to Bag 3 or be included in Bag 1 as shown.

FIG. 2 shows each compartment separately provided in a sterile bag with the carbohydrate compartment having a volume of 25 ml in Bag 2 and the buffered physiological compartment having a volume of 275 ml in Bag 1. The compartments may be combined by flow paths defined by plastic tubing 26, 22, to allow mixing of the compartments to form the synthetic medium in Bag 3. Alternatively each Bag 1 and Bag 2 could be individually connected to Bag 3 and the compartments mixed in Bag 3. Frangible connectors 24, 20 are provided to establish flow communication between the Bags of set 10.

FIG. 2A shows an alternative container system for combining the components of the storage solution described herein. As shown in FIG. 2A, container 70 preferably holds the buffered physiological components of citrate, acetate, phosphate, and potassium chloride. Container 72 preferably holds dextrose, sodium chloride, magnesium chloride and optionally calcium chloride. As shown in FIG. 2A, tubing 74a and 74b may include frangible connectors 75. Tubing 74a and 74b are joined at Y-connector 76. Tubing segment 78 downstream of connector 76 may be joined to a separate container (not shown) in which the components of containers 70 and 72 may be combined and to which bicarbonate may be added to arrive at the solution (PAS 5) described herein.

In one embodiment, containers 70 and 72 may include a combined volume of 300 ml (150 ml of solution in each of Container 70 and Container 72). The concentrations of the individual components in Containers 70 and 72 are selected so that upon combination, the combined aqueous solution has the concentration for each of the components as previously described. If desired, two units of 300 ml of storage solution may be combined. In other words, two container systems of the type shown in FIG. 2A may be attached to the separate container (not shown in FIG. 2A) to provide approximately 600 ml of the storage solution. Container systems of the type shown in FIG. 2A were utilized to prepare the storage solution (PAS 5) that was used in Studies 1-4 below. Of course, it will be understood that different containers and container systems may be used to arrive at the combined storage solution. For example, a single container having separate compartments separated by a frangible seal may also be used. An example of such a container is set forth in U.S. Patent Application Publication No. US20090214807, which is incorporated by reference herein.

Regardless of the container system used, once combined, the storage solution described herein (in 300 ml volume) may contain, for example, approximately 16.8 mM dextrose monohydrate (D-glucose), 0 or 1.0 mM calcium chloride, approximately 1.5 mM magnesium chloride, approximately 10 mM sodium citrate, approximately 30 mM sodium acetate, approximately 9.4 mM sodium phosphate (7.2 mM dibasic sodium phosphate anhydrous and 2.2 mM monobasic sodium phosphate dihydrate), approximately 5 mM potassium chloride, approximately 69.55 mM sodium chloride, and approximately 8-25 mM of sodium bicarbonate and more preferably approximately 10-20 mM.

The above-described aqueous storage solution may then be combined with platelets containing some amount of residual plasma, to yield a platelet product or suspension for storage with a plasma ratio for instance from about 10% to about 20%, and more preferably between about 1% and 10%, such as about 5%, and preferably less than about 5% and in other embodiments, less than 1%. Some methods of preparing platelets such as apheresis type collection or methods that involve washing steps may result in high concentrations of platelets with relatively small volumes of plasma. These methods will be described in further detail below. Consequently, in some cases, resuspension of the platelets for storage may require the addition of plasma as well as synthetic media.

Reduction of Residual Plasma in Platelet Concentrate

As generally illustrated in FIG. 9, the exemplary automated systems and methods described above may be used for reducing residual plasma from platelet concentrate. Preferably, an automated device that has been pre-programmed to perform desired processing procedures may be used to reduce plasma in platelet concentrate to obtain a desired platelet product.

In one embodiment, an apheresis device may include a programmable controller that is pre-programmed with one or more selectable protocols. A user/operator may select a particular processing protocol to achieve a desired outcome or objective, including, for example, to obtain a platelet product having a reduced plasma volume of approximately 5% of the total platelet product volume. The pre-programmed selectable protocol(s) may be based on several fixed and/or adjustable parameters, including, but not limited to, the volume of fluid being processed, volume of additive solution used or added to the platelets during processing, the desired platelet concentration, the desired volume of plasma to be removed, the processing time/duration of a given procedure and/or desired volume of final platelet product.

Once a particular protocol has been selected and a procedure initiated, the automated apheresis device may operate to perform one or more processing steps to reduce the amount of plasma from platelet concentrate until a desired plasma-reduced platelet product has been obtained.

For example, as shown in FIG. 9, an automated apheresis device may be used to perform a procedure that includes, but is not limited to, the steps of separating whole blood in a centrifugal separation chamber to obtain a platelet-rich component, separating plasma from the platelet-rich component in the same or different chamber to obtain a platelet concentrate, removing plasma from the platelet concentrate and reconstituting the platelet concentrate to obtain a platelet product with a desired reduced plasma volume.

Figure 5:
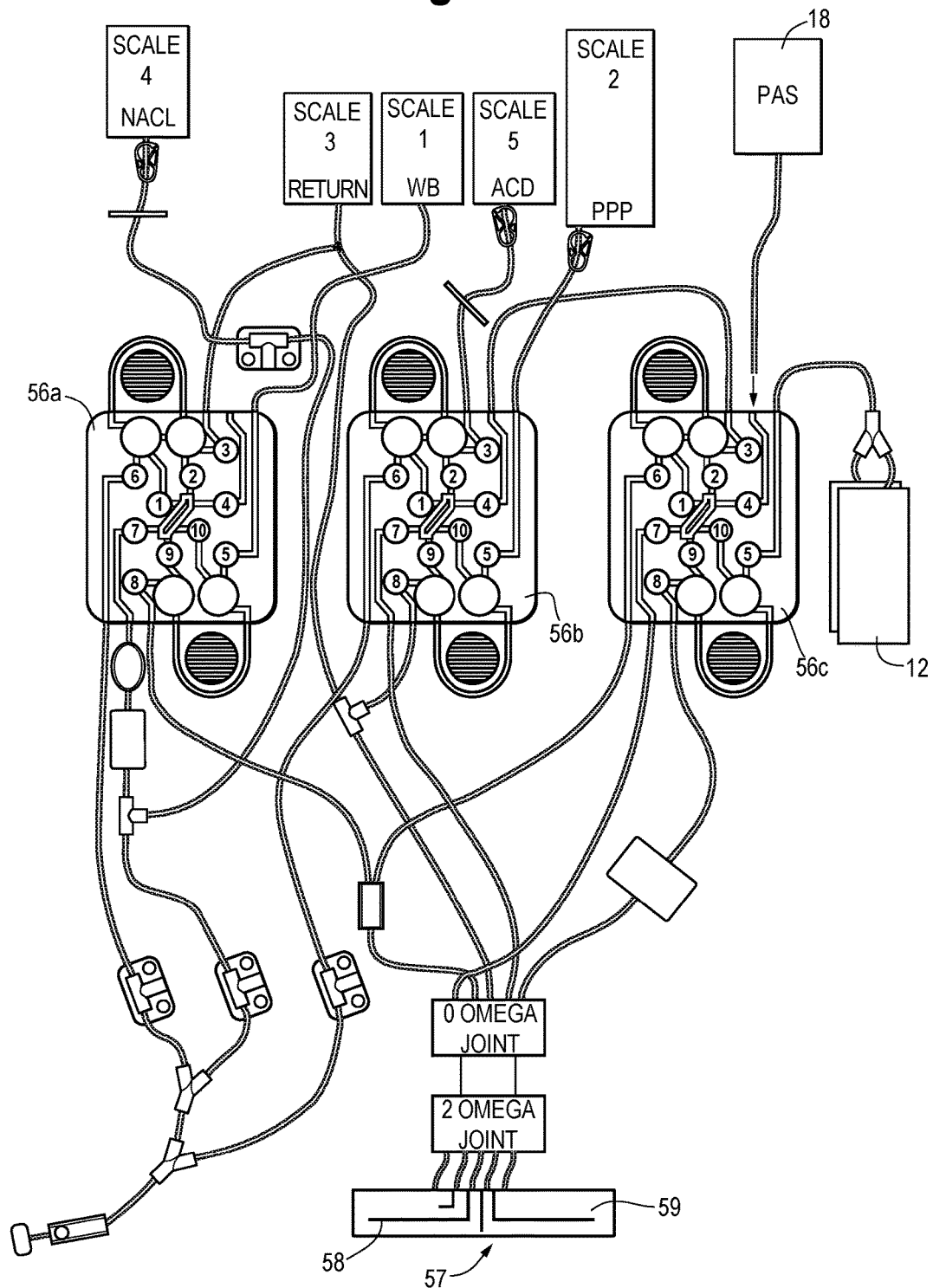
FIG. 5 is a diagram showing the disposable processing set of FIG. 4 with a container of the storage medium disclosed herein.

During a particular processing procedure, the pre-programmed controller may operate the centrifuge and processing chamber associated therewith to separate blood into its various components as well as operate one or more pumps to move blood, blood components and/or additive solution through the various openable valves and tubing segments of a processing set 54, such as the one illustrated in FIG. 5. This may include, for example, initiating and causing the centrifugal separation of platelets from whole blood in a separation chamber (or, more specifically, in a separation chamber of a processing chamber), removing plasma from platelets (i.e. pumping the removed plasma to a storage or waste bag) to obtain platelet concentrate, pumping additive solution, such as the synthetic aqueous storage solutions described above, from a source through selected valves and tubing segments to prime or purge the tubing segments and/or to displace fluid (such as plasma) that may reside or remain in the tubing during or after processing and combining additive solution with platelet concentrate in a concentration chamber to reconstitute platelet concentrate therein. The various processing steps performed by the pre-programmed automated apheresis device may occur separately, in series, simultaneously or any combination of these.

FIG. 5 diagrammatically illustrates one example of a disposable processing set or kit 54 that can be used with an apheresis device (such as the automated Amicus® Separator (centrifugal separation device) available from Fenwal, Inc. of Lake Zurich, Ill., and generally shown in FIGS. 3 and 4) for the separation and collection of platelets. Blood drawn from a volunteer donor may be centrifugally processed in separation sub-chamber 58 of processing chamber 57 to separate platelets from other blood components to obtain a platelet rich plasma suspension (i.e. platelets suspended in plasma). The platelet rich plasma may be conveyed from sub-chamber 58 to sub-chamber 59 where additional plasma may be removed to obtain platelet concentrate.

Platelet concentrate collected in sub-chamber 59 is relatively highly concentrated, as much of the plasma has been removed during the apheresis procedure for collection and/or return to the donor. However, it will be appreciated that the platelet concentrate still contains some residual amount of plasma. Further reduction of this plasma is desirable, such that upon resuspension of the platelet concentrate in an additive solution, the resulting platelet product comprises platelets suspended in approximately 5% plasma/95% additive solution (e.g., aqueous synthetic storage solution).

In one embodiment, the same separation device used to obtain the PC may also be used to reduce the residual plasma in the collected PC. Alternatively, an identical or other centrifugal separation device may be used to further process the PC to remove residual plasma. Regardless of whether the same or different separation device is used, one exemplary processing protocol that may be performed by an automated apheresis device for removing residual plasma from collected PC is illustrated in exemplary FIGS. 5A-5F, and described in further detail below. It will be appreciated that while the method described below may be performed using an Amicus® Separator, the method is not limited to any one type of separator. Thus, the order of steps and the volumes of fluids described below may vary depending on the device utilized.

Figure 6:
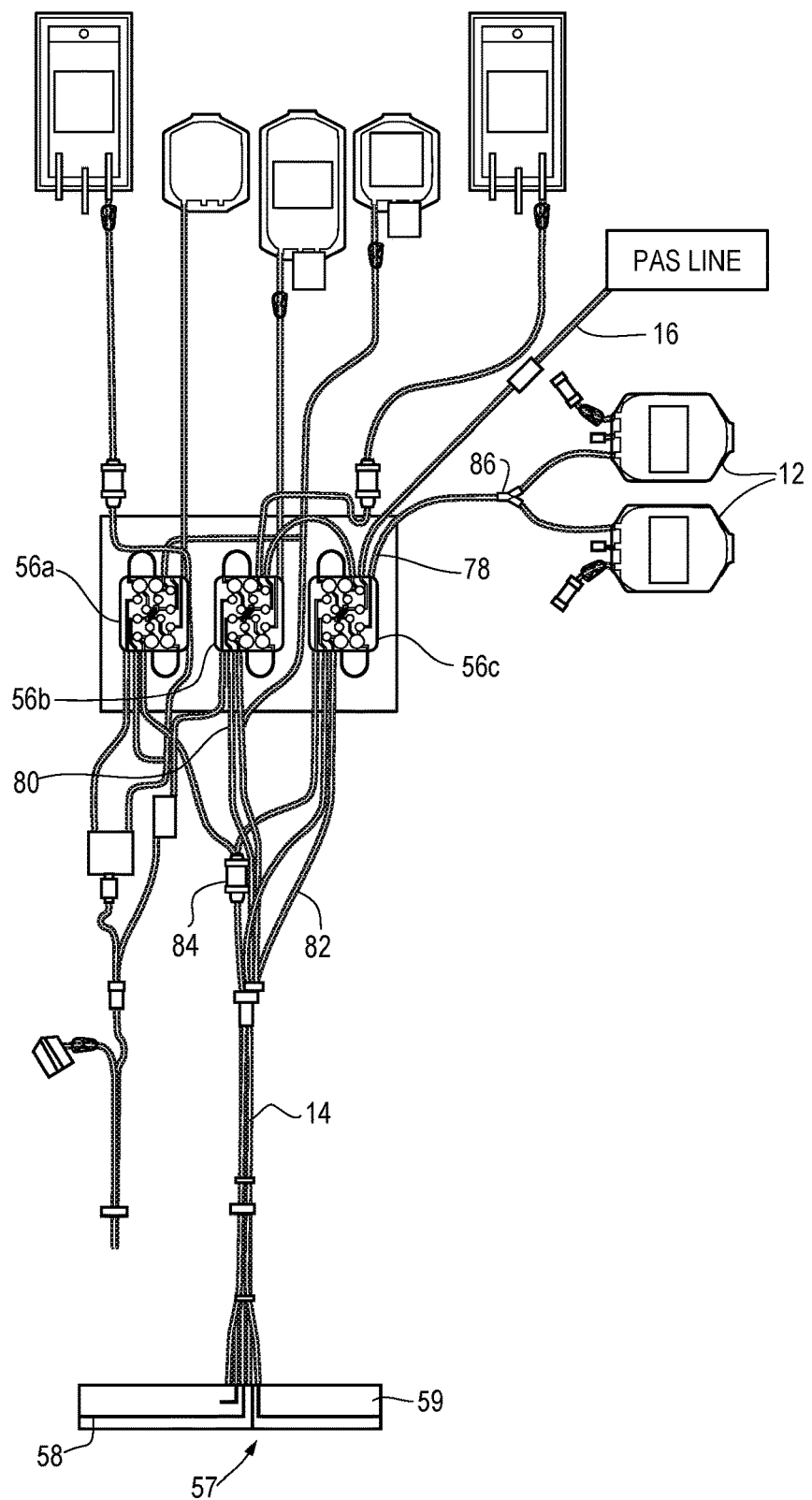
FIG. 6 is a diagram of the disposable processing set useful in another embodiment of the method of collecting and further processing platelets in accordance with the present disclosure.

With reference to FIG. 5, platelet concentrate has been collected in chamber 59 in an apheresis procedure and the donor disconnected. For example, concentrated platelets with residual plasma may reside in chamber 59 having a total volume of typically about 25 ml. A source of platelet additive solution (PAS) (such as the aqueous synthetic solutions described above) 18 is connected to the PAS line 16 (as also shown in FIG. 6), such as by sterile docking, so that the additive solution from source 18 is in flow communication with the various cassettes 56a, b, c, tubing flow paths and separation and collection chambers 58 and 59 of disposable kit 54. It will be understood that this additive solution may be any aqueous solution or media suitable for the preservation, storage and reconstitution of platelets, such as, but not limited to Intersol, PAS 3, PAS 4 or PAS 5, or other commercially available media. For the purposes of the present disclosure, such additive solutions or aqueous storage solutions 18 may hereinafter be referred to simply as "PAS".

Figure 5A:
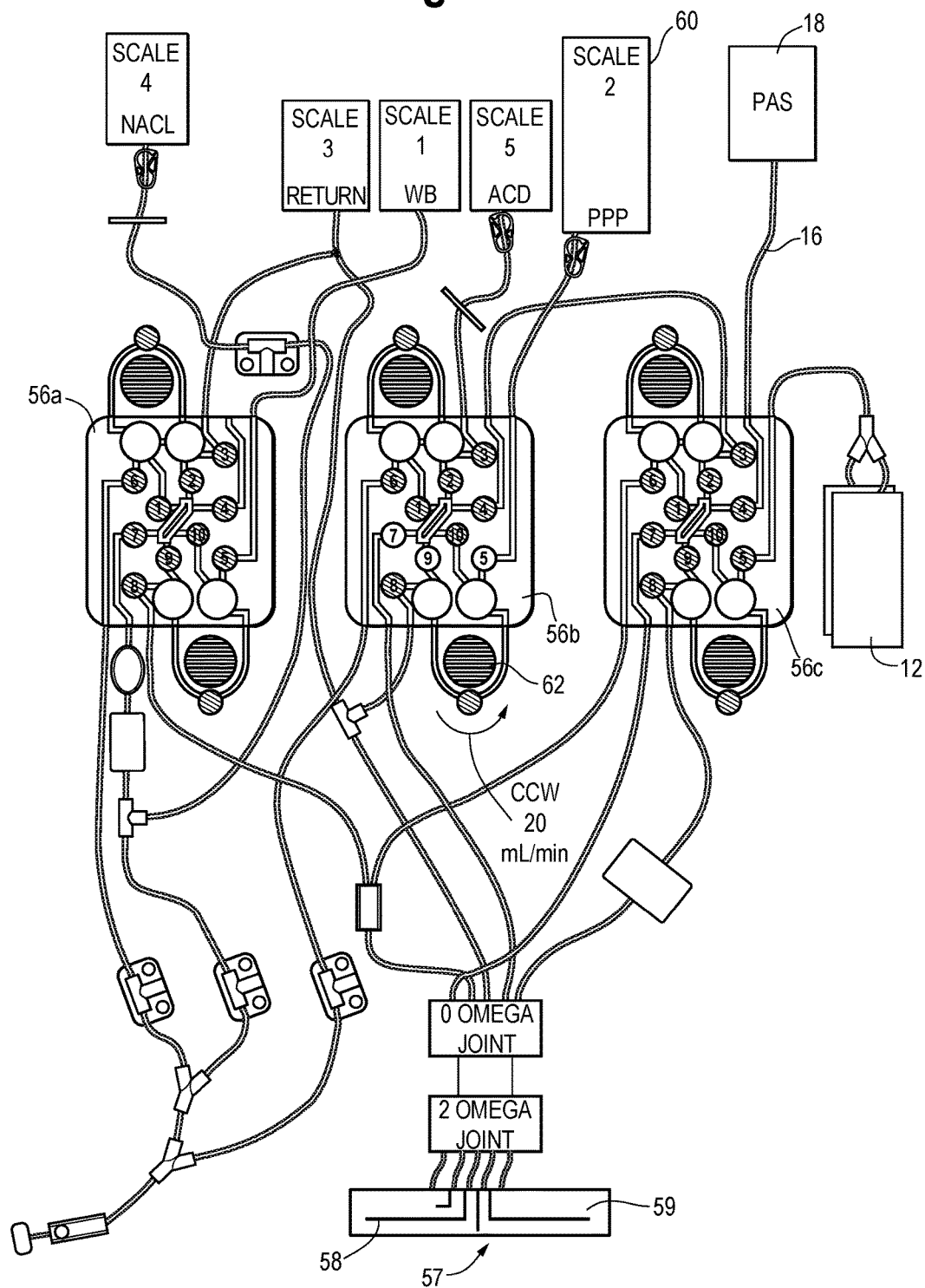
FIGS. 5A-5F are diagrams showing steps in the method of collecting and further processing of platelets in accordance with the present disclosure.

In accordance with one embodiment of a method for reducing residual plasma from PC approximately 10 ml of plasma may be removed from the platelet concentrate in chamber 59 and conveyed into plasma collection bag 60 as shown in FIG. 5A. For example, by operating a pump, such as pump 62 in a counter-clockwise direction, plasma is pumped from chamber 59, through the respective flow path segments and open valves of cassette 56b, and conveyed into plasma bag 60. In FIGS. 5, 5A-5F, valves 1-10 on each of cassettes 56(a)-(c) are shown as shaded, to indicate a closed valve or unshaded to indicate an open valve.

Figure 5B:
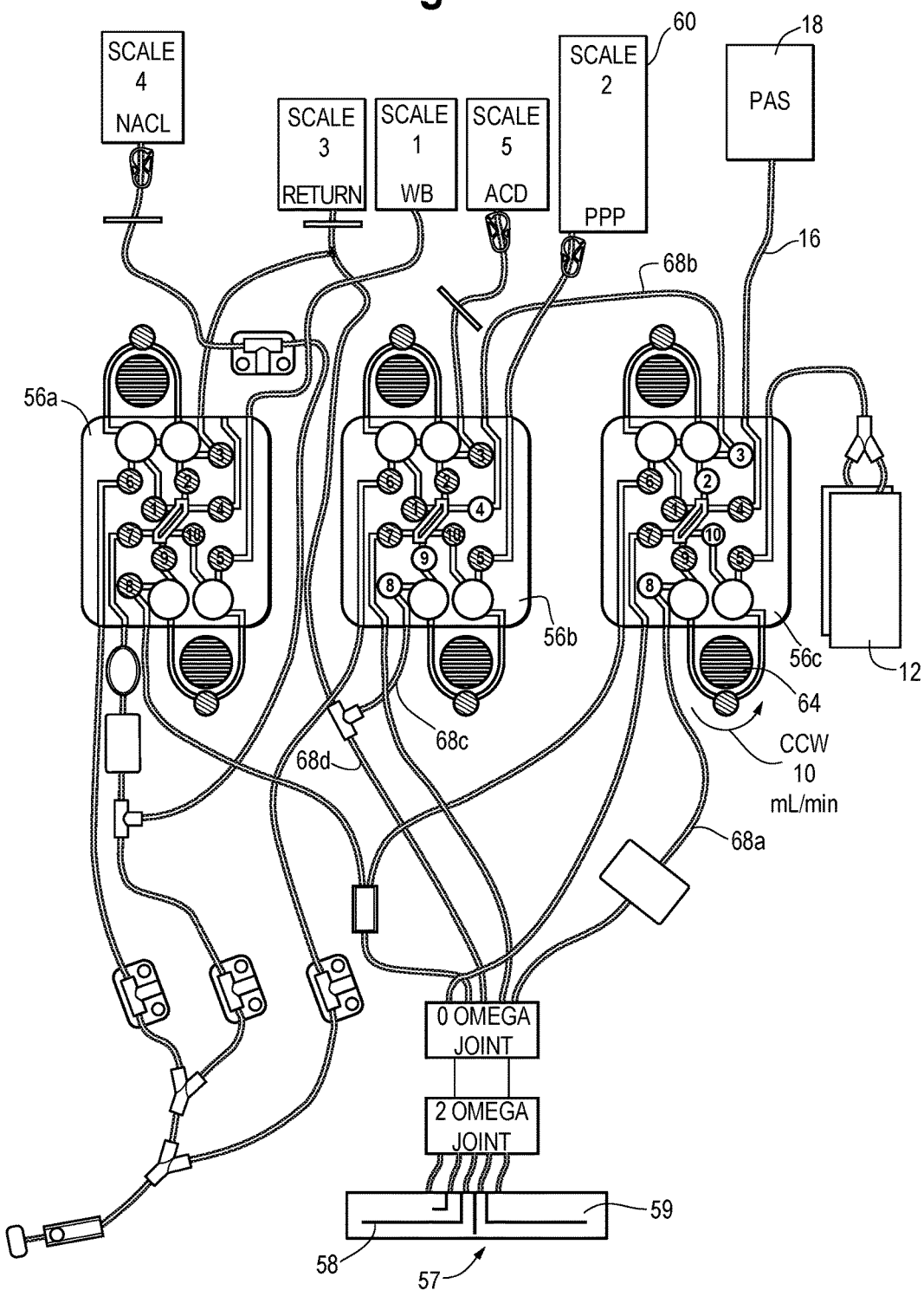
Figure 5C:
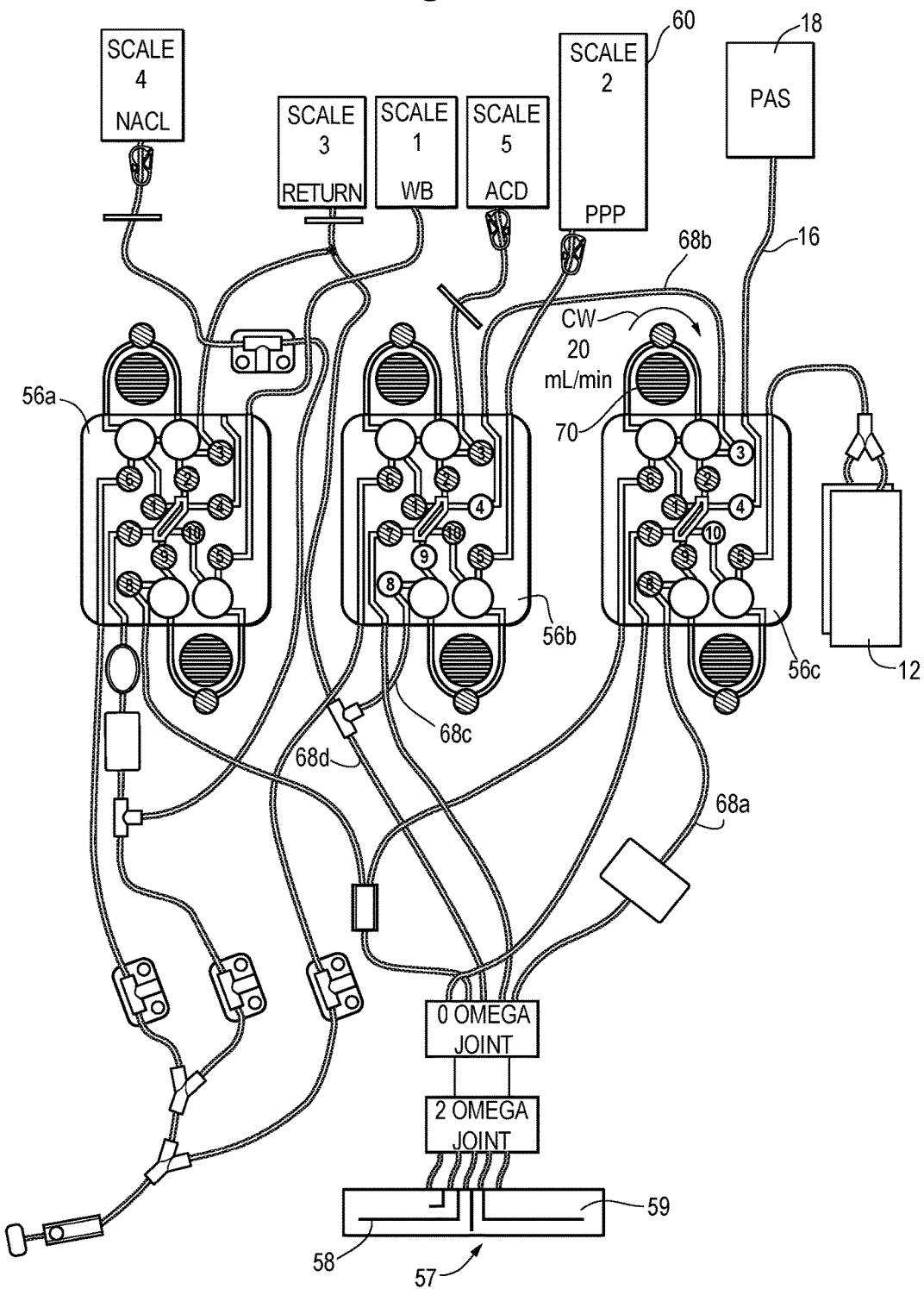

Next, as further illustrated in FIG. 5B, pump 64 of cassette 56c may be rotated (in a counter-clockwise direction) to pump fluid, such as plasma, remaining in one or more tubing segments such as tubing segments 68a, b, c and d following an apheresis procedure, to chamber 58. It will be appreciated that chamber 58, which served as a separation chamber for blood components during apheresis, will be substantially empty following the apheresis procedure, as blood and/or blood components, including platelets, have been conveyed out of chamber 58 and returned to the donor or conveyed into chamber 59, for example, for further processing. Thus, post-apheresis, sub-chamber 58 may serve as a "waste container" for receiving and containing excess fluid, blood components or other materials that are flushed out of the cassettes, tubing or other parts of processing kit 54. While fluid such as plasma is flushed out of tubing segments 68a, b, c and d and into sub-chamber 58, platelet concentrate remains in chamber 59 preferably undisturbed. The processing step of removing or flushing fluid, such as plasma, from tubing segments 68a, b, c and d and into chamber 58, as illustrated in FIG. 5B may be performed as an optional step, if desired.

Following the processing step shown in FIG. 5A and/or the optional step shown in FIG. 5B and described above, as shown in FIG. 5C, pump 70 may be rotated (for example, in a clock-wise direction) to pump approximately 20 ml of PAS from source container 18 into the flow path of cassette 56c, (through valves 4, 1 and 3 of cassette 56c) through tubing segment 68b and into the flow path of cassette 56b. The PAS then flows through the flow path segments of cassette 56b (through valves 4, 9 and 8) and is conveyed through tubing segments 68c and d, and into chamber 58. The step of pumping PAS from source 18 through cassettes 56c and 56b and into chamber 58 serves to flush out fluid, such as plasma, that may remain in the various tubing segments and valves of the cassettes 56b and 56c. This flushed plasma may be received by and held in (waste) sub-chamber 58, while platelet concentrate still remains in chamber 59 undisturbed.

Figure 5D:
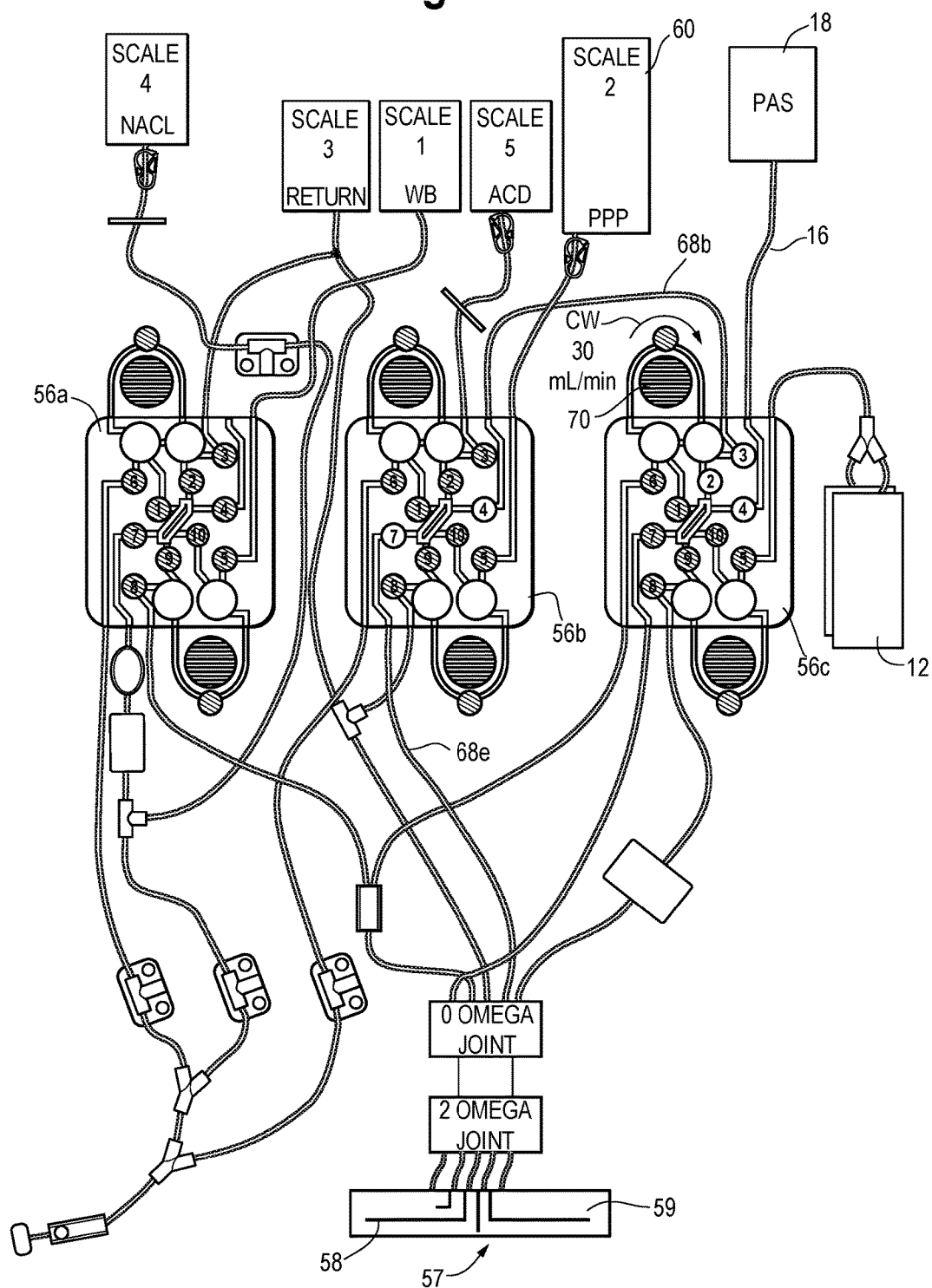

Next, as shown in FIG. 5D, pump 70 associated with cassette 56c is operated (in a clock-wise direction) to pump approximately 25 ml of PAS from source container 18 into chamber 59 in order to reconstitute platelet concentrate in chamber 59. The PAS from source 18 may flow through tubing segment 16 into cassette 56c (and through open valves 4, 2 and 3 of cassette 56c). From cassette 56c, the PAS may flow through tubing 68b, into cassette 56b (through open valves 4 and 7) through tubing segment 68e, where it is conveyed into sub-chamber 59.

Figure 5E:
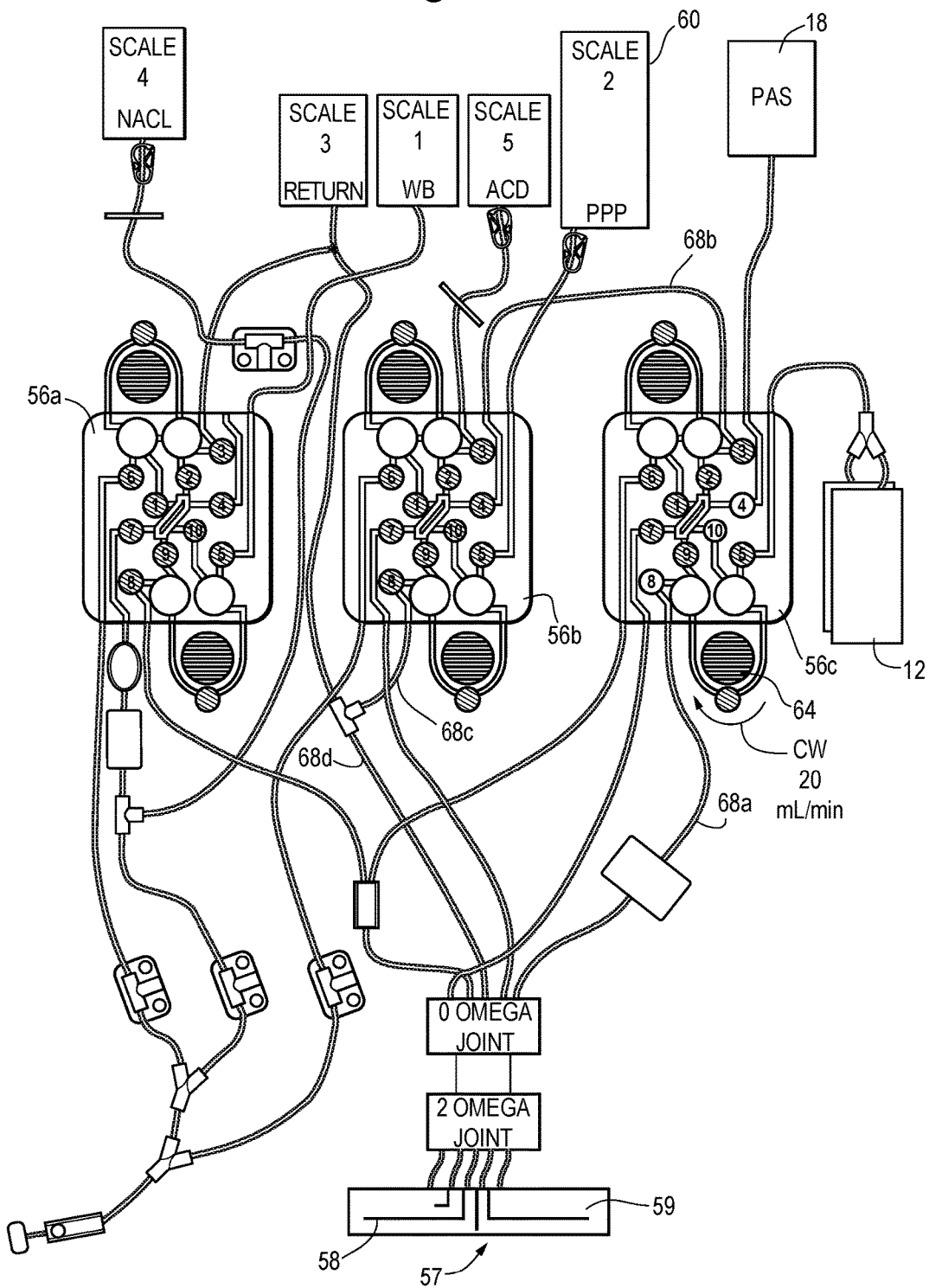

If the optional processing step illustrated in FIG. 5B is performed (i.e., plasma remaining in tubing segments 68a, b, c and d pumped to chamber 58), it is possible that some platelets may have been pulled out of chamber 59 and into tubing segment 68a by action of pump 64, (for example, pump 64 is operated for too long of a duration or too aggressively). Accordingly, in this instance, the further optional processing step illustrated in FIG. 5E may be employed. As shown in FIG. 5E, approximately 15 ml of PAS may be pumped from source container 18 through cassette 56c (through open valves 4, 10 and 8) and tubing segment 68a to push back any platelets that may have been pulled from chamber 59 into tubing 68a in the processing step illustrated in FIG. 5B into sub-chamber 59. This may be accomplished by operating pump 64 in a clock-wise direction. Any platelets pumped from tubing 68a back into chamber 59 may be reconstituted, or more specifically, resuspended with the platelet concentrate in chamber 59. Platelets, now combined with PAS may then be resuspended. Resuspension may be assisted by manual manipulation, massage or agitation of the platelet container by the operator, although other suitable methods of resuspension may be used including automated resuspension methods.

Figure 5F:
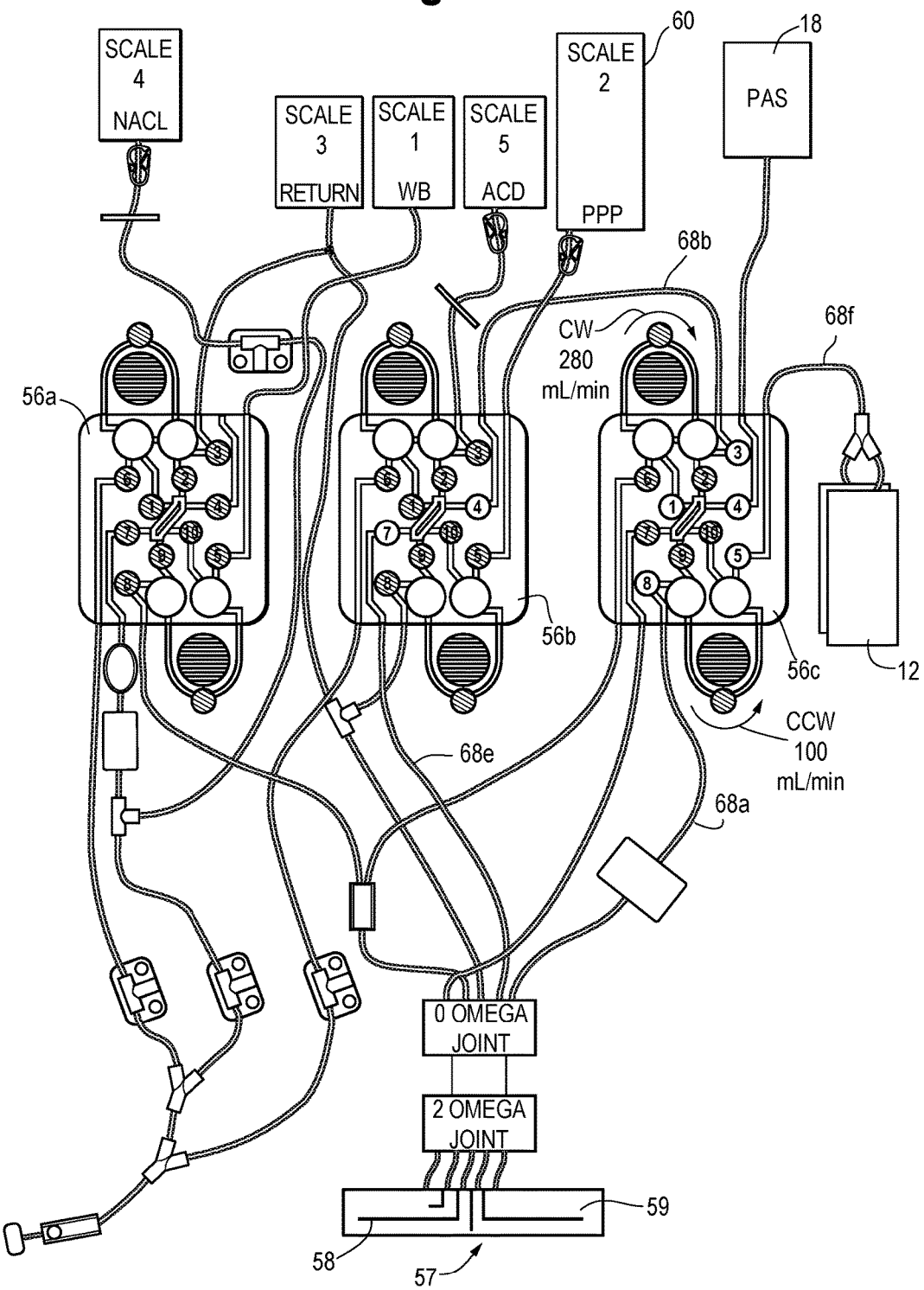

Next, platelets are transferred into storage containers 12 and combined with a sufficient volume of PAS to arrive at the desired percent volume of plasma. For example, as shown in FIG. 5F, approximately 570 ml of PAS may be pumped from source container 18 through cassette 56c (through open valves 4, 1 and 3) and into chamber 59 by operating pump 70 in a clock-wise direction and pump 64 in a counter-clockwise direction. In particular, PAS may be conveyed into the flow path of cassette 56c (through open valves 4, 1 and 3) through tubing segment 68b, into cassette 56b (through open valves 4 and 7), through tubing segment 68e and into chamber 59. Platelets are flushed by the PAS from chamber 59 into storage container 12. Specifically the platelets flow out of chamber 59 into tubing segment 68a, into cassette 56c (through open valves 8 and 5), through tubing segment 68f and into storage container 12. In one embodiment, the platelets are suspended in 570 ml of PAS and approximately 30 ml of plasma, preferably, in two separate containers, each having platelets suspended in approximately 285 ml of PAS and 15 ml of plasma, resulting in a platelet product of platelet concentrate suspended in approximately 5% plasma/95% PAS-5, suitable for storage and/or transfusion.

As noted above, the apparatus and systems shown in FIGS. 3 and 4 and described in the above-identified patents and published applications are examples of suitable apparatus and systems for collecting and/or otherwise providing (in an automated fashion) platelets in a reduced volume of plasma. Other systems wherein platelets are concentrated in a separation chamber and/or collected outside of such chamber may also be used. Concentrated platelets that are collected outside of the separation chamber may be reconstituted in, for example, an external but attached container to provide an initial platelet product with some residual plasma. If reductions to or below 5% plasma are desired, the collected platelets may be reintroduced into the separation chamber to reduce volume of plasma accordingly, including to or below 1% by washing.

While the steps described above have been described as part of one continuous procedure (after the donor has been disconnected), it will be appreciated that these steps may be carried out intermittently and in multiple passes until the desired amount of platelets has been collected. Thus, for example, a volume of whole blood may be collected and the platelets separated, reconstituted and transferred to a collection container in the manner described above with the donor still connected, and additional whole blood can be collected and the steps described above, repeated.

Automated Systems and Methods for Providing Washed Platelet Concentrate

The exemplary automated systems and methods described above are useful for reducing the residual volume of plasma from PC collected in an apheresis procedure to obtain a platelet product (i.e. platelets suspended in platelet storage media and plasma) wherein the volume of plasma has been reduced to approximately 5% or less of the total platelet product volume. However, it may also be desirable to even further reduce the amount of plasma in platelet concentrate. Such further plasma reduction may be achieved by "washing" platelet concentrate.

As with the systems and methods described above for reducing residual plasma from platelet concentrate to obtain a platelet product containing less than 5% plasma, automated systems and methods of the type described above may also be used for further washing platelet concentrate to obtain a platelet product having less than 1% plasma. As illustrated by the method identified by reference numeral 120 in FIG. 9, platelet concentrate may be washed after apheresis is complete or "post-apheresis". This may include washing platelets immediately following an apheresis procedure using the same automated separation device in which the PC was obtained, or washing previously collected platelets from another source, such as a different separation device or platelets from a storage container. Alternatively, as also shown in FIG. 9, in one embodiment, platelet concentrate can be washed as part of, or during, an apheresis procedure (method 200).

Washing Post-Apheresis

In one embodiment, platelet concentrate may be obtained in an apheresis procedure using the Amicus® Separator or other separation device, reconstituted in additive solution and held in a collection container 12, in accordance with the methods described above and as shown in FIGS. 5A-5F (e.g., preferably after the donor has been disconnected) and referenced as method 100 in FIG. 9. The resuspended platelet concentrate may then be washed using an automated separation device, such as the Amicus® Separator or other device.

For example, one or more sources of platelets, such as resuspended platelet concentrate in container(s) 12 that were collected with the Amicus® Separator or other suitable device in accordance with the methods described above, may be connected through a junction, such as a "Y" connector, to a new sterile disposable processing set 54, and the set loaded on to an Amicus® Separator (or other device). A source of wash solution, such as a PAS solution including those described herein (e.g., PAS-5), may also be connected though a junction to processing set 54. Using the Amicus® or other suitable device, a wash procedure (referred to by reference numeral 120 in FIG. 9) may be initiated, for example, by selecting a particular pre-programmed protocol to achieve a desired outcome. In a preferred embodiment, a washed platelet concentrate that upon reconstitution, will result in a platelet product having a volume of plasma that is less than about 1% of the total platelet product volume may be provided.

Once the desired protocol has been selected, the automated washing procedure may be initiated, such that platelet concentrate (with reduced plasma) from source container(s) 12 may be drawn into, and concentrated in a centrifugal field, in chamber 59. Washing fluid such as a PAS, may be drawn into chamber 59 while a centrifugal field is maintained. As the procedure progresses and wash solution is continuously fed through chamber 59 to displace and push the plasma out, the proportion of plasma in the fluid removed from the chamber is reduced, as it is replaced by an increasing proportion of wash (e.g., PAS) solution.

Once a washing procedure is complete, the washed platelet concentrate residing in collection chamber 59 may then be resuspended in a selected volume of a resuspension fluid (e.g., PAS). Resuspension may be performed using any suitable resuspension method, such as manual manipulation of chamber 59 as previously described. The resuspension fluid may be the same as the wash solution, or may be a different fluid suitable for platelet resuspension and/or storage. In a preferred embodiment, both the wash solution and the resuspension fluid is a synthetic platelet additive solution, such as PAS-5 described above. If desired, the resuspended washed platelets may be harvested by transferring them to a container for storage, transfusion, or further processing. In one example, this may be accomplished by conveying additional wash solution through chamber 59, to thereby flush the resuspended washed platelets into a storage container.

Washing During or as Part of Apheresis

Alternatively, in accordance with the systems and methods described herein, platelets may be washed as part of an apheresis procedure. Washing platelets during, or as part of an apheresis procedure may be accomplished using separation devices such as the Amicus® Separator, or by other known automated separation devices as indicated by reference numeral 200 in FIG. 9. In particular, washing may be performed while platelets are being separated from whole blood into platelet rich plasma in a centrifugal field. As described above, a platelet rich suspension is separated from other blood components in a centrifugal field, for example, in separation chamber 58 (using, for example, the Amicus® Separator shown in FIGS. 3 and 4). The platelet rich suspension is conveyed into chamber 59 where plasma is continuously removed from the chamber 59 while the centrifugal field is maintained. It will be appreciated that as plasma is continuously removed, platelets become increasingly concentrated in chamber 59.

In one embodiment, a selected volume of plasma may be removed from the platelets in collection chamber 59 such that the platelets are considered to be "hyper-concentrated". In one example, "hyper concentrated platelets" may include, but are not limited to, platelets having a concentration that is higher than that at which platelets are typically stored. For example, the concentration of stored platelets may typically be less than 2 million platelets per microliter ($\mu L$), such as in the range of approximately 1.3 to 2 million platelets/$\mu L$, whereas hyper-concentrated platelets may have a concentration of greater than 2 million platelets/$\mu L$.

Regardless of whether platelets are washed to a point at which they are considered "hyper-concentrated" (to a concentration of greater than about 2 million platelets/μL) or washed to a lesser extent (to a concentration of less than about 2 million platelets/μL), the systems and methods for washing platelets in accordance with the present disclosure are essentially the same. For example, plasma is being removed from collection chamber 59 during apheresis, wash solution, including, but not limited to, aqueous solutions such as saline, platelet additive solution (PAS-5, PAS-4, PAS-3, Intersol or any other suitable synthetic media) may be continuously added to chamber 59 to help displace or "wash" plasma out of the chamber 59, while platelets remain in the chamber.

In one example, up to 100 ml of wash solution, such as PAS-5 or other PAS may be added to chamber 59 while a centrifugal field is maintained. Plasma is thereby pushed out of the chamber by the wash solution as it is continuously added and then removed from chamber 59, while platelets remain in the chamber. Thus, it will be appreciated that at the beginning of a given wash procedure, the majority of the fluid removed from chamber 59 is plasma. However, as the procedure progresses and wash solution is continuously fed through the chamber to displace and push the plasma out, the proportion of plasma in the fluid removed from the chamber is reduced, as it is replaced by an increasing proportion of wash solution. At or near the end of a given wash procedure, the fluid removed from chamber 59 is typically largely wash solution. This procedure may be repeated one or more times, as necessary.

The wash procedure may be terminated once it has been determined that the desired volume of plasma has been removed, and the platelets concentrated to a desired level. In one example, the automated separation device used to perform the wash procedure may be pre-programmed into the software-driven controller of the apheresis device to conduct a particular selectable wash procedure or "protocol". In other words, the device may be pre-programmed with one or more platelet collection and/or washing protocol(s) from which a user may select, based on the user's objective or desired outcome for a particular procedure, such as reducing the plasma in the platelet concentrate to obtain a washed platelet product having less than approximately 1% plasma. As previously mentioned, the pre-programmed selectable protocol(s) may be based on several fixed and/or adjustable parameters, including, for example, the volume of fluid being processed, volume of wash solution used, desired platelet concentration, the desired volume of plasma to be removed, the processing time/duration of a given procedure and/or desired volume of final platelet product.

In any event, once it has been determined that the platelet washing procedure is complete (i.e. when the selected protocol has ended and/or one or more of the above-mentioned objectives has been achieved), the washed platelet concentrate may reside in collection chamber 59. The washed platelet concentrate may then be resuspended in a selected volume of fluid. The resuspension fluid may be the same as the wash solution, or may be a different fluid suitable for platelet resuspension. In a preferred embodiment, both the wash solution and the resuspension fluid is a synthetic platelet additive solution, such as PAS-5. The resuspended washed platelets may, if desired, be transferred to a container for storage, transfusion, or further processing.

By way of example, but not limitation, illustrations of systems and methods of removing plasma from platelet concentrate and for storing platelets using the storage media described herein are provided below.

EXAMPLES

Two in vitro evaluations of platelet concentrates suspended in 5% plasma/95% PAS-5 were performed. In Study 1, 5% plasma/95% PAS-5 platelets were prepared directly on the Amicus® Separator, with no additional offline washing steps performed. This procedure is similar to the collection of 35% plasma/65% PAS-3 platelets on the Amicus® Separator. However, it does not allow for collection of a paired 100% plasma control, so an alternate procedure was used for the second evaluation. In Study 2, hyper-concentrated platelets in plasma were collected using the Amicus® Separator, followed by an additional centrifugation step to achieve paired platelet products in 100% plasma and in 5% plasma/95% PAS-5.

PAS-5 Solution Preparation

PAS-5 was prepared on the day of platelet collection by mixing separate salt and glucose solutions provided a dual bag assembly of the type shown in FIG. 2A, into a transfer pack (PL1813, Fenwal Inc., Lake Zurich, Ill.). This combined solution (600 ml, pH 7.3) contained (in mM concentrations): 9.99 $Na_3$-citrate; 30.0 Na-acetate; 2.2 $NaH_2PO_4$; 7.2 $Na_2HPO_4$; 69.4 NaCl, 5.0 KCl; 1.5 $MgCl_2$; 1.0 $CaCl_2$ and 16.8 glucose. Sodium bicarbonate (6 ml of 7.5% solution, Mediatech, Inc; Manassas, Va.) was then added through a sterile medication port by syringe transfer through a sterile filter (0.22 μm filter, Sarstedt, Inc., Newton, N.C.). The resulting PAS-5 solution (pH 7.6-7.7) was thoroughly mixed.

Study 1

Platelet Preparation

Double platelet products were collected from volunteer donors using the Amicus® Separator, as shown generally in FIGS. 3 and 4, (software v3.2, Fenwal Inc., Lake Zurich, Ill.), and acid-citrate-dextrose Formula A (ACD-A) anticoagulant with a whole blood:anticoagulant ratio of 10:1. A double platelet product was collected with a target platelet yield of $6.0-8.0 \times 10^{11}$ platelets and collecting between 100-500 ml total plasma volume. FIG. 5 is a diagram of the disposable processing set used with the Amicus® apheresis device.

After the donor was disconnected from the apheresis device, the centrifuge pack was not removed from the Amicus® spool. The lines leading to the ACD and saline bags were heat sealed and the bags removed from the kit. The kit was loaded onto another Amicus® device. PAS 5 container 18 was attached to the kit as shown in FIG. 5. Additional processing steps are shown and described above with reference to FIGS. 5A-5F. Platelets were transferred to the platelet storage containers by flushing PAS-5 through the collection chamber and into the platelet storage containers 12. The resulting platelet concentrates contained approximately 5% plasma/95% PAS-5 in 300 ml total volume per each product. After resting for 2 hours at 20-24° C., the platelet units were transferred to a horizontal agitator (Helmer, model PC2200; Noblesville, Ind.) for storage at 20-24° C. Only one platelet unit was evaluated from each pair.

Platelet Assay

Apheresis platelet units were sampled aseptically using a syringe on Days 1 and 7 of storage. Day 5 samples were also collected when available. Approximately 5 ml were withdrawn from each platelet unit on each day of sampling. Platelet concentration and mean platelet volume were determined using a hematology analyzer (KX-21N, Sysmex America Inc., Mundelein, Ill.). Platelet content was calculated by multiplying the platelet concentration by the platelet product volume (weight of unit/specific gravity of PAS, 1.01) measured the same day. An automated gas analyzer (Bioprofile pHOx, Nova Biomedical, Waltham, Mass.) was used to measure platelet pH, $pO_2$, and $pCO_2$ at 37° C. Bicarbonate concentration and pH at 22° C. were automatically calculated from these measurements. Glucose, lactate and lactate dehydrogenase were determined spectrophotometrically (AU400E, Olympus America, Inc., Center Valley, Pa.). Morphology score was performed after the method of Kunicki et al., with the addition of an altered disc category, Kunicki T J, Tuccelli M, Becker, G A, Aster, R H., "A Study of Variables Affecting the Quality of Platelets Stored in Room Temperature." *Transfusion,* 1975; 15(5):414-21. Hypotonic shock response (HSR) was measured turbimetrically (SPA 2000, Chrono-Log Corp., Havertown, Pa.), Holme, S. et al., "A Multi-Laboratory Evaluation of In Vitro Platelet Assays: the Tests for Extent Shape Change and Response to Hypotonic Shock." Biomedical Excellence for Safer Transfusion Working Party of the International Society of Blood Transfusion. *Transfusion,* 1998; 38(1):31-40. HSR samples were diluted with refrigerated autologous plasma (pre-warmed to room temperature before addition to samples) and test sample blanks were made using the same concentration of PAS-5 as in the diluted sample. Total protein concentration in the concurrent plasma and platelet concentrate supernatant were determined using a protein assay based on Coomassie Blue staining (Bio-Rad Protein Assay Kit, Bio-Rad Laboratories, Hercules, Calif.). Plasma fraction was calculated from total protein concentration in the platelet concentrate supernatant divided by total protein concentration in the concurrent plasma.

Study 2

Platelet Preparation

An Amicus® double apheresis unit was collected from a donor by ARC Research Blood Program with a targeted yield of $7.6 \times 10^{11}$ platelets in 198 ml plasma using a single needle procedure, Amicus® software v 3.2 and acid-citrate-dextrose Formula A (ACD-A) anticoagulant with a whole blood:anticoagulant ratio of 10:1. A concurrent plasma volume of 320 ml was also collected. A total of 12 double units with concurrent plasma were collected and used for Study 2 (n=12).

Platelets were allowed to rest without agitation at 20-24° C. for 4 hours. The double unit was divided equally into the two supplied, 1 L containers 12 (FIG. 5) by weight. Two hundred ml of concurrent (autologous) plasma was sterile docked to one of the PL-2410 containers and transferred to one unit (Control) using a sterile connection device (TSCD model SC-201A, Terumo Transfusion Products, Somerset, N.J.). Two hundred ml of PAS-5 was similarly transferred to the other PL-2410 container. Both units were then centrifuged at 4161×g (3800 rpm, Sorval RC3BP+, Thermo Scientific, Waltham, Mass.) at 20 to 24° C. and with an accumulated centrifugal effect (ACE) of $5.5 \times 10^7$. All but approximately 35-40 ml of PAS-5/plasma were expressed from the Test unit. From the Control unit, sufficient plasma was expressed, leaving 250 ml remaining plasma volume. Fresh PAS-5 was added to the platelet pellet immersed in PAS-5/plasma to yield a 250 ml volume of approximately 5% plasma/95% PAS-5. Platelets were then resuspended immediately and both units were rested for 1 hour without agitation at 20-24° C. prior to being placed on an agitator (Helmer, model PC900i, Noblesville, Ind., 70 cycles/minute) for 20-24° C. storage.

Platelet Assay

All apheresis platelet units were sampled by syringe on the mornings of Days 1, 5 and 7. Approximately 5-6 ml were withdrawn from each platelet unit on each day of sampling. Platelet concentration and mean platelet volume (MPV) were determined using a hematology analyzer (Cell Dyn 3700, Abbott, Abbott Park, Ill.), and platelet content was calculated by multiplying the platelet concentration by the platelet volume (weight of the unit/specific gravity, 1.03 for plasma and 1.01 for PAS) measured the same day. Measurements of pH were performed at room temperature (20-24° C.) using an Orion meter (Thermo Scientific, Beverly, Mass.)/Accu-pHast combination pH electrode (Fisher Scientific, Pittsburgh, Pa.). The platelets were assayed for $pO_2$, $pCO_2$, glucose, and lactate were measured at 37° C. using a blood gas/blood chemistry analyzer (Cobas, Roche b 221, Indianapolis, Ind.). Bicarbonate was automatically calculated from these measurements. Platelet morphology was assessed by phase microscopy as the percentage of platelets with discoid morphology. Extent of shape change (ESC) and hypotonic stress response (HSR) were measured turbimetrically (SPA2000 Chronolog, Havertown, Pa.), Holme, S., et al., ESC and HSR samples and blanks were prepared as described in Study 1. The extent of platelet activation was measured on freshly stained samples using flow cytometry (FacsCalibur, BD Biosciences, San Jose, Calif.) with antibodies to CD61, CD62P, CD63 and their isotype controls, Curners, J., et al., "Flow Cytometric Measurement of CD 62P (P-selectin) expression on platelets: a Multicenter Optimization and Standardization Effort." *Transfusion,* 2008; 48:1439-1446. Percent plasma in each platelet concentrate was measured as described in Study 1.

Statistical Analysis

The data which appear in Tables 3-4 below represent mean levels with standard deviations for the various platelet parameters. Determination of means, standard deviations of experimental values and performance of ANOVA with repeated measures were carried out using standard statistical software (Instat, GraphPad Software, San Diego, Calif.).

TABLE 3

Platelet storage parameters in suspensions containing 5% plasma/95% PAS-5 (Study 1)

|  | Day 1 | Day 5* | Day 7 |
|---|---|---|---|
| Platelet count (×10³/μL) | 1009 ± 157 | 1039 ± 134 | 1032 ± 154 |
| Platelet content (×10¹¹)† | 3.03 ± 0.49 | 2.99 ± 0.41 | 2.89 ± 0.45 |
| MPV (fL) | 7.7 ± 0.5 | 7.6 ± 0.6 | 7.7 ± 0.6 |
| pH (22° C.) | 7.44 ± 0.06 | 7.51 ± 0.07 | 7.50 ± 0.09 |
| Glucose (mg/dL)† | 295 ± 10 | 265 ± 12 | 243 ± 13 |
| Lactate (mM)† | 1.7 ± 0.5 | 5.1 ± 1.2 | 7.2 ± 1.7 |
| Bicarbonate (mM) | 9.8 ± 0.5 | 9.7 ± 1.2 | 9.4 ± 1.3 |
| pCO₂ (mm Hg) | 23.0 ± 2.8 | 19.4 ± 2.4 | 19.3 ± 2.9 |
| pO₂ (mm Hg) | 75.1 ± 18.7 | 89.9 ± 16.0 | 98.1 ± 18.5 |
| LDH (U/L) | 68 ± 39 | 76 ± 29 | 91 ± 32 |
| HSR (%) | 59.2 ± 12.0 | 54.5 ± 6.5 | 55.0 ± 10.1 |
| Morphology (0-400)† | 353 ± 20 | 319 ± 14 | 302 ± 18 |

Values represent mean ± 1 SD;
n = 12,
*n = 9,
†p ≤ 0.005

TABLE 4

Platelet storage parameters in suspensions containing 100% plasma (Control) and 5% plasma/95% PAS-5 platelet (Test) (Study 2)

|  | Day 1 | Day 5 | Day 7 |
|---|---|---|---|
| Platelet count (×10³/μL) | | | |
| Control | 1466 ± 113 | 1450 ± 134 | 1434 ± 130 |
| Test | 1411 ± 121* | 1443 ± 137 | 1410 ± 128 |

TABLE 4-continued

Platelet storage parameters in suspensions containing 100% plasma (Control) and 5% plasma/95% PAS-5 platelet (Test) (Study 2)

|  | Day 1 | Day 5 | Day 7 |
|---|---|---|---|
| Platelet content ($\times 10^{11}$) | | | |
| Control | 3.79 ± 0.31 | 3.66 ± 0.36 | 3.54 ± 0.34 |
| Test | 3.62 ± 0.32* | 3.61 ± 0.36 | 3.46 ± 0.33 |
| MPV (fL) | | | |
| Control | 7.01 ± 1.02 | 7.37 ± 0.84 | 7.33 ± 0.92 |
| Test | 7.03 ± 0.99 | 7.01 ± 1.03 | 7.11 ± 1.20 |
| pH (22° C.) | | | |
| Control | 7.24 ± 0.09 | 7.25 ± 0.14 | 7.13 ± 0.12 |
| Test | 7.23 ± 0.10 | 7.24 ± 0.19 | 7.21 ± 0.18 |
| Glucose (mg/dL) | | | |
| Control | 292 ± 19 | 215 ± 26 | 179 ± 31 |
| Test | 282 ± 10 | 227 ± 18 | 202 ± 25 |
| Lactate (mM) | | | |
| Control | 5.9 ± 0.8 | 13.4 ± 2.1 | 17.1 ± 2.3 |
| Test | 2.8 ± 0.6* | 8.0 ± 2.1* | 11.0 ± 3.0* |
| Bicarbonate (mM) | | | |
| Control | 18.5 ± 1.5 | 11. ± 1.8 | 8.6 ± 2.0 |
| Test | 10.1 ± 0.5* | 9.5 ± 1.8* | 8.9 ± 2.5 |
| pCO$_2$ (mm Hg) | | | |
| Control | 56.9 ± 6.1 | 33.9 ± 2.9 | 31.7 ± 4.0 |
| Test | 25.9 ± 2.8* | 23.0 ± 2.4* | 22.5 ± 2.8* |
| pO$_2$ (mm Hg) | | | |
| Control | 98.4 ± 13.6 | 106.9 ± 13.4 | 111.1 ± 13.5 |
| Test | 96.1 ± 13.0 | 108.7 ± 13.6 | 114.3 ± 15.2 |
| ESC (%) | | | |
| Control | 25.5 ± 7.4 | 22.0 ± 5.6 | 19.8 ± 5.5 |
| Test | 17.3 ± 11.5* | 15.1 ± 7.6* | 13.5 ± 8.0* |
| HSR (%) | | | |
| Control | 60.7 ± 16.9 | 61.2 ± 13.6 | 57.4 ± 14.1 |
| Test | 65.5 ± 20.1 | 64.1 ± 12.9 | 55.1 ± 12.7 |
| Morphology (% discs) | | | |
| Control | 67 ± 15 | 55 ± 15 | 49 ± 16 |
| Test | 69 ± 13 | 60 ± 13 | 56 ± 13 |
| CD62P (% positive platelet) | | | |
| Control | 51.9 ± 15.6 | 45.7 ± 9.8 | 52.3 ± 11.7 |
| Test | 52.1 ± 14.8 | 39.5 ± 10.8* | 41.8 ± 13.1* |
| CD63 (% positive platelet) | | | |
| Control | 19.0 ± 10.7 | 23.3 ± 10.1 | 24.1 ± 8.9 |
| Test | 18.4 ± 10.2 | 19.5 ± 9.7 | 18.4 ± 7.5* |

Values represent mean ± 1 SD;
n = 12;
*p ≤ 0.001 for Test versus Control

Study 3

In this study, the in vitro storage of platelet concentrates with 5% plasma/95% PAS 5 was studied for up to 14 days. Platelets were collected and samples assayed in the manner described in connection with Study 1 Platelets were stored in a "high" (pH approximately 7.6-7.7) pH 95% PAS 5/5% plasma medium and a "low" (pH approximately 7.4) pH 95% PAS 5/5% plasma medium. Results are included in Tables 6, 7, 8 and 9 set forth below.

Study 4

In this study, a manual protocol was used to produce Amicus® double platelet products in 5% plasma/95% PAS-5 (Table 5). A standard Amicus® double platelet collection was performed using a US approved InterSol® kit, as generally shown in FIG. 6. After the donor was disconnected from the device, the umbilicus assembly, "PAS" line and platelet storage containers 12 were heat sealed off from the kit. The PAS line and platelet storage containers were then sterile connected to the umbilicus assembly 14. PAS-5 was connected onto the PAS line 16 and was used to resuspend the platelets as well as to transfer the platelets to the platelet storage containers. The resulting 5% plasma platelet concentrates (300 ml each) were stored for up to 14 days with in vitro testing performed on Days 0, 1, 5, 7, 9, and 14.

TABLE 5

Composition of PAS 5

| Composition (g/L) | PAS-5 (w/ calcium) |
|---|---|
| Na$_3$Citrate•2H$_2$O | 2.91 |
| Na Acetate•3H$_2$O | 4.04 |
| NaH$_2$PO$_4$•2H$_2$O | 0.35 |
| NaH$_2$PO$_4$ | 1.01 |
| NaCl | 4.02 |
| KCl | 0.37 |
| MgCl$_2$ | 0.30 |
| Glucose | 3.30 |
| CaCl$_2$ | 0.15 |
| Na Bicarbonate | 0.83 |

Eight evaluable, double platelet products were collected and studied using standard in vitro assays. An evaluable product was defined as one that had been collected in 5% plasma/95% PAS-5 and had generated the in vitro parameter results required per this protocol at Days 0, 1, 7 and 14 at a minimum. Two, 300 ml dual bag assemblies as shown in FIG. 2A of the solution set forth in Table 5, but without bicarbonate (and divided among containers 70 and 72 as previously described) were required for each double platelet product collection. First, the two dual bag assemblies (FIG. 2A) were pooled into a 1000 ml transfer pack with inline injection site. Then, bicarbonate solution was added through the injection site and the solution was mixed and sampled for pH.

Amicus® Collection Procedure

The current Amicus® operator's manual instructions were followed for single and double needle platelet collections. A double platelet product was collected with a target of 6.0-8.0*10$^{11}$ platelets, ACD ratio of 10:1 and between 100-700 ml total plasma volume collected.

Post-Collection Kit Modification

With reference back to FIG. 6, the PPP line 80 and PRP line 82 were labeled at a location near the umbilicus with black indelible marker. All of the tubing lines leading to the umbilicus were heat sealed at a location approximately in line with the bottom of the drip chamber 84 (as shown in FIG. 6). The PAS line 16 was heat sealed near the cassette 56c port, as shown in FIG. 6 and disconnected from the kit. The collection chamber/umbilicus assembly was disconnected from the kit. The double platelet product and approximately 30 ml of plasma remained in this assembly. The tubing leading to the platelet storage containers was heat sealed at approximately 6 inches from the "Y" 86, as also shown in FIG. 6 and disconnected from kit.

Platelet Concentrate Preparation

Figure 7:
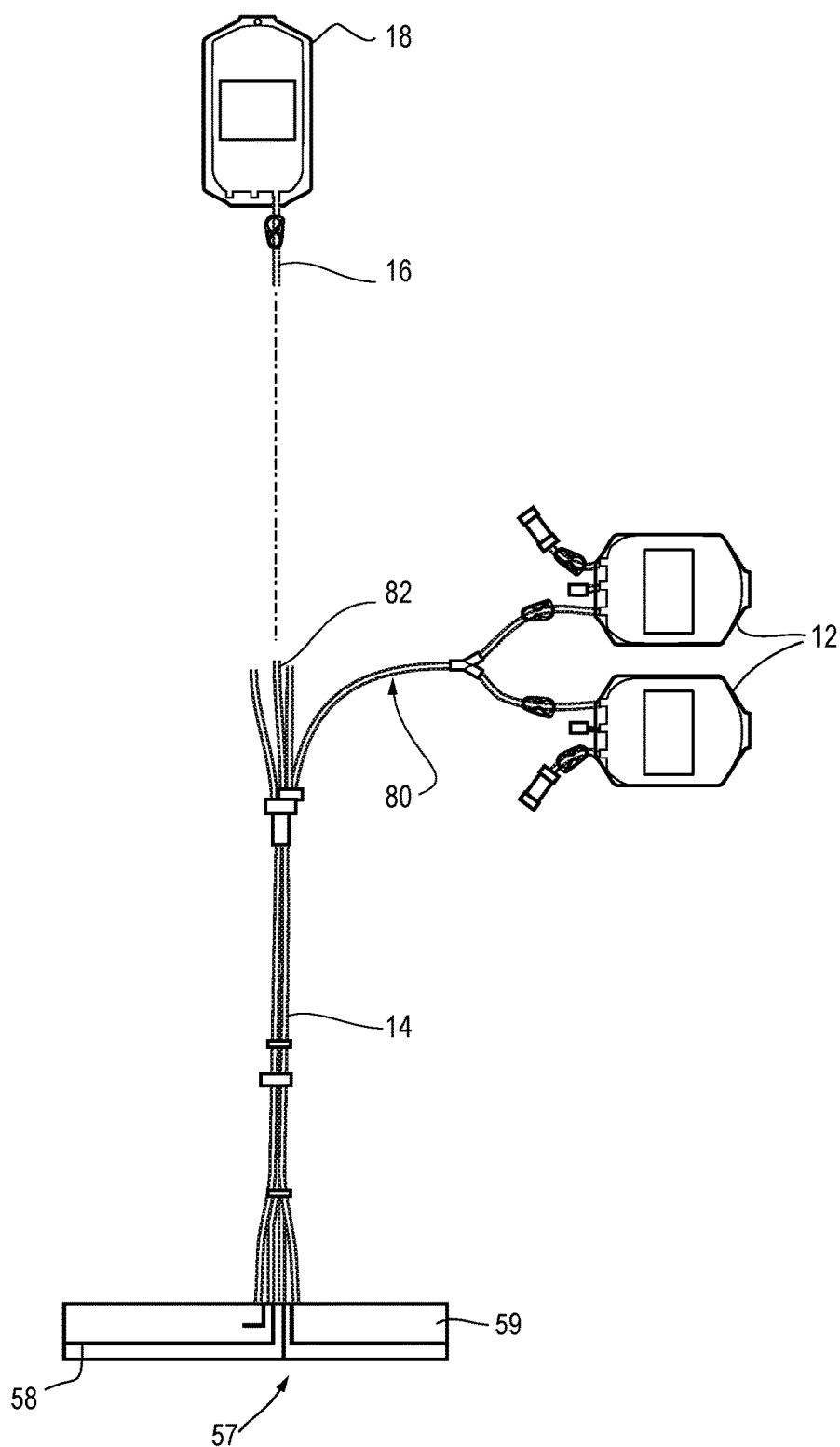
FIG. 7 is a diagram showing additional steps of the method of FIG. 6.
Figure 8:
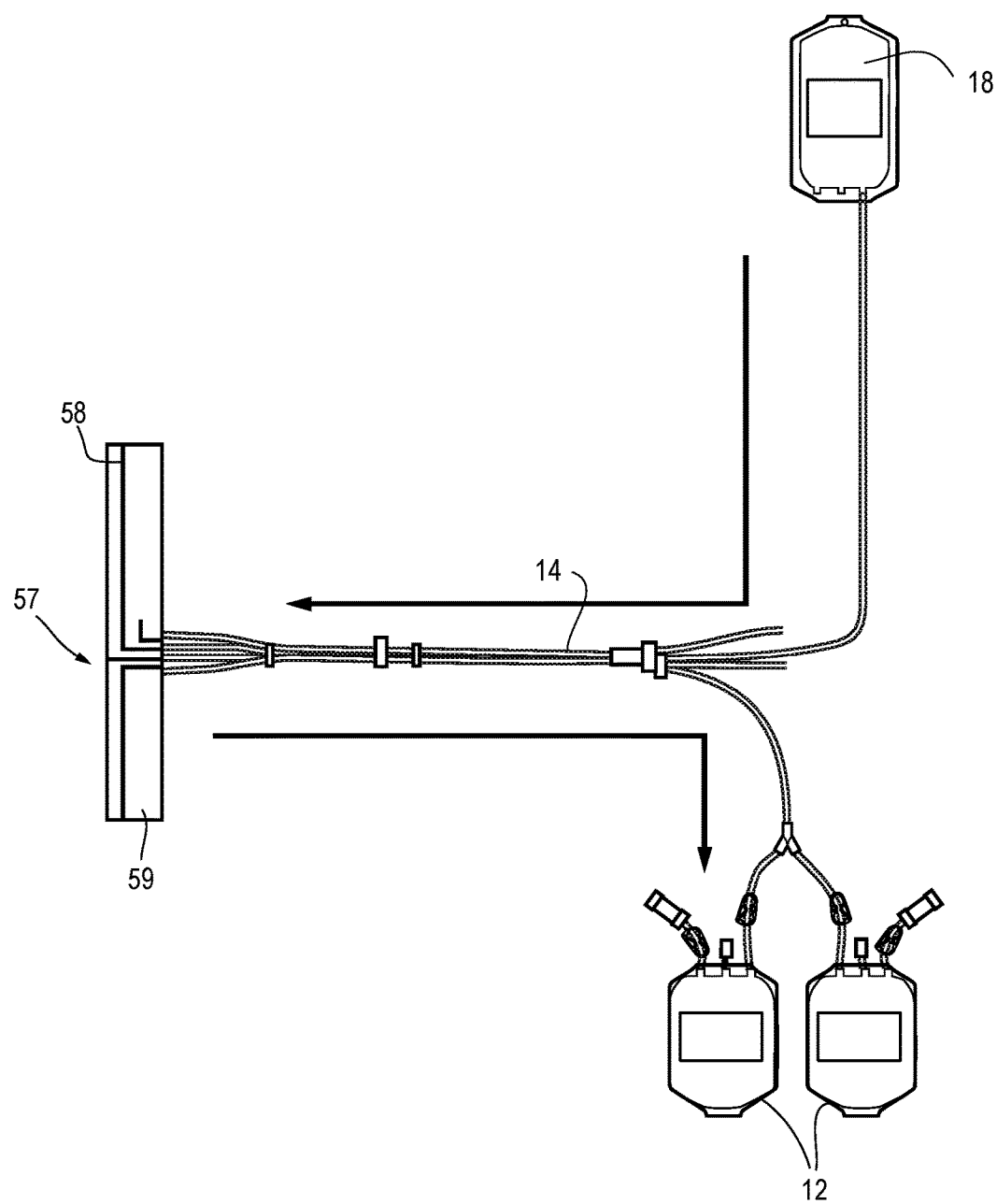
FIG. 8 is a diagram showing a further step of the method of FIGS. 6 and 7.

The PAS-5 solution was sterile connected onto the PAS line 16 in the correct orientation (arrow on filter pointing in the direction of fluid flow). The opposite end of the PAS line was sterile connected to an empty 150 ml transfer pack. The filter and PAS line were primed with PAS-5 to remove any air in the assembly and the line was heat sealed approximately 6 inches below the filter. The line was primed with just enough PAS-5 to clear air from the PAS line. An excess amount of PAS-5 was not used for priming as the majority of the volume was needed for platelet storage. The clamp was closed on each tubing line leading to a platelet storage container. The two platelet storage container assembly was sterile connected to the PPP line 80 (as shown in broken lines in FIG. 7). The PAS-5 line was sterile connected to the PRP line 82 (as shown by the broken line in FIG. 7). A hemostat was placed on the line in between the sterile filter and umbilicus. The hemostat was opened on the PAS line and approximately 20-30 ml of PAS-5 was drained into the collection chamber 58. The hemostat on the PAS line was closed. The platelets were resuspended manually per Amicus® operator's manual. One of the platelet storage containers was placed on a scale and the storage container was used to tare the scale. The hemostat on the PAS line was opened. The clamp leading to the platelet storage container on the scale was opened. PAS-5 solution was drained through the collection chamber and into the open platelet storage container 12 until the scale read approximately 605±10 g, at which time, the hemostat on the PAS line was closed. Note: For optimal draining, the collection chamber was hung vertically at a height below the PAS-5 solution and above the platelet storage containers as shown in FIG. 8. A blood bag spike injection site was inserted into each storage container and a sample was removed for total protein analysis.

Storage

The platelet concentrates were stored under standard blood bank conditions, i.e. with continuous agitation at 20-24° C. in PL 2410 suitable platelet storage containers until the end of storage. On Day 0, 1, 7 and 14 at a minimum and on Day 5 and 9 when possible, the products were removed from storage and mixed thoroughly. The bag weights were recorded prior to sampling.

In Vitro Testing

Samples were analyzed on Day 0, 1, 7 and 14 at a minimum and on Day 5 and 9 when possible, for the following parameters:

a) Platelet concentration and platelet MPV
b) White blood cell count
c) pH, $pO_2$, $pCO_2$, $HCO_3$
d) Glucose, lactate, LDH
e) Swirling—Bertolini method, Transfusion (34) 796-801, 1994
f) Hypotonic Shock Response
g) Morphology score
h) Extent of Shape Change
i) CD62 (p-selectin)
j) Bacterial testing using Verax Biomedical Incorporated Platelet PGD® Test A sample of the PPP (platelet poor plasma) from each collection was analyzed for total protein content (g/dL). A sample of each platelet concentrate was assayed for total protein content (mg/dL) using the Bio-Rad Quick Start Bradford Protein Assay kit, Product #500-0202, following manufacturer's instructions.

Results

Results from Studies 3 and 4 are set forth in the following Tables 6-9. PAS-5L and PAS-5H refer to the storage of platelets in "low" and "high" pH PAS 5 of Study 3. PAS-5 refers to the solution and storage medium used in Study 4.

Data for in vitro storage parameters and percent plasma in each unit were entered into Excel worksheets. All data and formulas were verified manually.

TABLE 6

Bicarbonate concentration and pH of PAS(s)

| PAS Solutions | PAS-5 | PAS-5 L | PAS-5 H |
|---|---|---|---|
| Bicarbonate (mM) | 10 | 20 | 20 |
| pH | 7.60 | 7.45 | 7.70 |

TABLE 7

Platelet unit characteristics on Day 1

| Storage Solution | Volume (ml) | Platelet Count ($\times 10^3/\mu L$) | Plasma Ratio (%) |
|---|---|---|---|
| PAS-5* | 294 ± 10 | 1228 ± 149 | 4.0 ± 0.4 |
| PAS-5 L | 300 ± 5 | 1130 ± 135 | 4.8 ± 0.8 |
| PAS-5 H | 298 ± 6 | 1130 ± 147 | 4.5 ± 0.4 |

Values represent mean ± SD,
n = 10,
*n = 8

TABLE 8

Blood gas parameters on day 0, 1, 7 and 14 of storage

| | Day 0 | Day 1 | Day 7 | Day 14 |
|---|---|---|---|---|
| pH (22° C.) | | | | |
| PAS-5 | 7.43 ± 0.03 | 7.43 ± 0.06 | 7.55 ± 0.04 | 7.42 ± 0.11 |
| PAS-5 L | 7.35 ± 0.03 | 7.56 ± 0.05 | 7.74 ± 0.06 | 7.63 ± 0.10 |
| PAS-5 H | 7.52 ± 0.04 | 7.65 ± 0.06 | 7.77 ± 0.06 | 7.67 ± 0.12 |
| $HCO_3^-$ (mM) | | | | |
| PAS-5* | 10.7 ± 0.3 | 10.6 ± 0.6 | 12.6 ± 1.2 | 9.2 ± 2.4 |
| PAS-5 L | 19.5 ± 0.9 | 17.8 ± 0.7 | 17.5 ± 1.4 | 14.1 ± 2.7 |
| PAS-5 H | 20.1 ± 0.9 | 19.4 ± 0.9 | 18.9 ± 2.1 | 15.1 ± 3.4 |
| $pO_2$ (mmHg) | | | | |
| PAS-5* | 160 ± 35 | 43 ± 16 | 66 ± 16 | 92 ± 17 |
| PAS-5L | 81 ± 15 | 47 ± 16 | 69 ± 16 | 94 ± 16 |
| PAS-5H | 82 ± 15 | 45 ± 15 | 71 ± 18 | 94 ± 18 |

Values represent mean ± SD,
n = 10,
*n = 8

TABLE 9

In vitro parameters after 1, 7, and 14 days of storage

| | Day 1 | Day 7 | Day 14 |
|---|---|---|---|
| MPV (fL) | | | |
| PAS-5* | 8.0 ± 0.5 | 7.8 ± 0.4 | 8.1 ± 0.5 |
| PAS-5 L | 7.7 ± 0.4 | 7.5 ± 0.4 | 7.7 ± 0.4 |
| PAS-5 H | 7.7 ± 0.4 | 7.5 ± 0.4 | 7.7 ± 0.4 |
| Morphology (0-400) | | | |
| PAS-5* | 353 ± 10 | 312 ± 14 | 269 ± 14 |
| PAS-5 L | 364 ± 11 | 315 ± 14 | 275 ± 20 |
| PAS-5 H | 361 ± 12 | 312 ± 19 | 273 ± 21 |

TABLE 9-continued

In vitro parameters after 1, 7, and 14 days of storage

|  | Day 1 | Day 7 | Day 14 |
|---|---|---|---|
| HSR (%) | | | |
| PAS-5* | 76 ± 10 | 64 ± 10 | 56 ± 8 |
| PAS-5 L | 71 ± 11 | 62 ± 11 | 59 ± 19 |
| PAS-5 H | 72 ± 12 | 59 ± 9 | 57 ± 20 |
| ESC (%) | | | |
| PAS-5* | 28 ± 4 | 21 ± 3 | 14 ± 3 |
| PAS-5 L | 28 ± 4 | 21 ± 2 | 15 ± 5 |
| PAS-5 H | 27 ± 3 | 22 ± 2 | 16 ± 4 |
| CD62p (%) | | | |
| PAS-5* | 26 ± 7 | 20 ± 7 | 31 ± 11 |
| PAS-5 L | 26 ± 8* | 18 ± 5† | 27 ± 6‡ |
| PAS-5 H | 26 ± 8* | 20 ± 3† | 25 ± 7‡ |
| LDH(U/L) | | | |
| PAS-5* | 51 ± 20 | 62 ± 16 | 126 ± 66 |
| PAS-5 L | 57 ± 16 | 75 ± 18 | 105 ± 21 |
| PAS-5 H | 58 ± 19 | 74 ± 17 | 107 ± 25 |

Values represent mean ± SD,
n = 10,
*n = 8,
†n = 7,
‡n = 5

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. An automated method of washing platelets during apheresis comprising:
   a) operating an automated separation device comprising a centrifuge including a separation chamber and a concentration chamber;
   b) introducing a blood product including at least platelets and residual plasma into said separation chamber of said centrifuge device;
   c) separating said platelets and residual plasma from said blood product in said separation chamber,
   d) introducing said separated platelets and residual plasma into said concentration chamber while continuing to separate platelets and residual plasma from said blood product in said separation chamber;
   e) subjecting said platelets within said concentration chamber to a centrifugal field to obtain a platelet concentrate;
   f) introducing a wash solution into said concentration chamber of said separation device;
   g) continuing to subject said platelet concentrate to said centrifugal field during said introduction of said wash solution;
   h) displacing said residual plasma from said concentration chamber by said introduction of said wash solution; and
   i) removing residual plasma from said chamber to provide a washed platelet product comprising platelets, wash solution and plasma, wherein the volume of plasma in said washed platelet product is 1% or less of the total washed platelet product.

2. The method of claim 1 comprising sequentially introducing two or more batches of said blood product wherein each sequential introduction is followed by said separation, said wash solution introduction and said removal step to arrive at said volume of plasma.

3. The method of claim 1 further comprising introducing said wash solution into said concentration chamber while simultaneously removing plasma from said concentration chamber.

4. The method of claim 1 further comprising collecting said platelet concentrate in a collection container and reintroducing said platelet concentrate from said collection container into said concentration chamber.

5. The method of claim 1 comprising removing plasma such that the concentration of platelets is greater than about 2 million platelets per µL.

6. The method of claim 1 comprising introducing said blood product from a donor in fluid communication with said separation device.

7. A method of washing platelets during apheresis comprising:
   a) operating a centrifugal apheresis device having a separation chamber and a concentration chamber;
   b) concentrating platelets suspended in plasma in said concentration chamber of said apheresis device to obtain concentrated platelets suspended in a reduced volume of plasma;
   c) collecting substantially all of said concentrated platelet suspension;
   d) removing residual plasma remaining in said apheresis device;
   e) re-suspending said concentrated platelets in a volume of aqueous additive solution, wherein said aqueous additive solution comprises:
      from about 45 to about 120 mM sodium chloride;
      from about 5 to about 15 mM sodium citrate;
      from about 20 to about 40 mM sodium acetate;
      from about 0.05 to about 12 mM phosphate;
      from about 0.05 to about 3 mM magnesium ion;
      from about 0.05 to about 10 mM potassium chloride;
      from about 5 to about 40 mM sodium bicarbonate; and
      from about 0.5 to about 20 mM glucose; and
   f) conveying said resuspended concentrated platelets into said concentration chamber of said apheresis device to remove additional plasma from said concentrated platelet suspension to provide a concentrated platelet product comprising platelets, said aqueous additive solution and plasma, wherein the volume of plasma in said platelet product is less than 5% of the total platelet product volume.

8. The method of claim 7 wherein the volume of plasma in said platelet product is 1% or less of the total platelet product volume.

9. The method of claim 8 further comprising introducing a wash solution into said concentration chamber.

10. The method of claim 8 further comprising subjecting said resuspended concentrated platelet to a centrifugal field.

11. The method of claim 10 comprising introducing a wash solution into said concentration chamber while subjecting said resuspended concentrated platelet to said centrifugal field.

12. The method of claim 11 wherein said wash solution is said platelet additive solution.

* * * * *